(12) United States Patent
Drmanac

(10) Patent No.: US 12,227,803 B2
(45) Date of Patent: *Feb. 18, 2025

(54) METHODS AND COMPOSITIONS FOR EFFICIENT BASE CALLING IN SEQUENCING REACTIONS

(71) Applicant: Complete Genomics, Inc., San Jose, CA (US)

(72) Inventor: Radoje Drmanac, Los Altos Hills, CA (US)

(73) Assignee: Complete Genomics, Inc., San Jose, CA (US)

( * ) Notice: Subject to any disclaimer, the term of this patent is extended or adjusted under 35 U.S.C. 154(b) by 319 days.

This patent is subject to a terminal disclaimer.

(21) Appl. No.: 17/523,706

(22) Filed: Nov. 10, 2021

(65) Prior Publication Data

US 2022/0275442 A1 Sep. 1, 2022

Related U.S. Application Data

(63) Continuation of application No. 15/359,277, filed on Nov. 22, 2016, now Pat. No. 11,214,832, which is a
(Continued)

(51) Int. Cl.
*C12P 19/34* (2006.01)
*C12Q 1/686* (2018.01)
(Continued)

(52) U.S. Cl.
CPC .......... *C12Q 1/6874* (2013.01); *C12Q 1/686* (2013.01); *C12Q 1/6869* (2013.01);
(Continued)

(58) Field of Classification Search
USPC ....... 435/6.1, 6.11, 6.12, 91.1, 91.2; 436/94, 436/501; 536/23.1, 24.3, 24.33
See application file for complete search history.

(56) References Cited

U.S. PATENT DOCUMENTS 4,719,179 A  1/1988 Barany
4,863,879 A  9/1989 Kwok
(Continued)

FOREIGN PATENT DOCUMENTS

CN  101570784 A  11/2009
EP   0805190 A2  11/1997
(Continued)

OTHER PUBLICATIONS

U.S. Appl. No. 16/882,461, Final Office Action mailed On Dec. 29, 2021, 16 pages.
(Continued)

*Primary Examiner* — Frank W Lu
(74) *Attorney, Agent, or Firm* — Kilpatrick Townsend & Stockton LLP

(57) ABSTRACT

The present invention is directed to methods and compositions for acquiring nucleotide sequence information of target sequences. In particular, the present invention provides methods and compositions for improving the efficiency of sequencing reactions by using fewer labels to distinguish between nucleotides and by detecting nucleotides at multiple detection positions in a target sequence.

6 Claims, 12 Drawing Sheets

Specification includes a Sequence Listing.

Related U.S. Application Data continuation of application No. 14/094,630, filed on Dec. 2, 2013, now Pat. No. 9,523,125, which is a continuation of application No. 12/361,507, filed on Jan. 28, 2009, now Pat. No. 8,617,811.

(60) Provisional application No. 61/024,396, filed on Jan. 29, 2008, provisional application No. 61/024,110, filed on Jan. 28, 2008.

(51) Int. Cl.
  *C12Q 1/6869* (2018.01)
  *C12Q 1/6874* (2018.01)
  *C12Q 1/6876* (2018.01)
  *C12Q 1/68* (2018.01)

(52) U.S. Cl.
  CPC ............ *C12Q 1/6876* (2013.01); *C12Q 1/68* (2013.01); *C12Q 2565/102* (2013.01); *C12Q 2565/1025* (2013.01)

(56) References Cited

U.S. PATENT DOCUMENTS

| | | |
|---|---|---|
| 4,883,750 A | 11/1989 | Whiteley et al. |
| 5,091,302 A | 2/1992 | Newman et al. |
| 5,124,246 A | 6/1992 | Urdea et al. |
| 5,143,854 A | 9/1992 | Pirrung et al. |
| 5,202,231 A | 4/1993 | Drmanac et al. |
| 5,302,509 A | 4/1994 | Cheeseman |
| 5,354,668 A | 10/1994 | Auerbach |
| 5,403,708 A | 4/1995 | Brennan et al. |
| 5,405,747 A | 4/1995 | Jett et al. |
| 5,426,180 A | 6/1995 | Kool |
| 5,427,930 A | 6/1995 | Birkenmeyer et al. |
| 5,436,130 A | 7/1995 | Mathies et al. |
| 5,474,796 A | 12/1995 | Brennan |
| 5,508,169 A | 4/1996 | Deugau et al. |
| 5,525,464 A | 6/1996 | Drmanac et al. |
| 5,547,839 A | 8/1996 | Dower et al. |
| 5,632,957 A | 5/1997 | Heller et al. |
| 5,641,658 A | 6/1997 | Adams et al. |
| 5,648,245 A | 7/1997 | Fire et al. |
| 5,667,971 A | 9/1997 | Hochberg |
| 5,710,000 A | 1/1998 | Sapolsky et al. |
| 5,714,320 A | 2/1998 | Kool |
| 5,728,524 A | 3/1998 | Sibson |
| 5,728,528 A | 3/1998 | Mathies et al. |
| 5,744,305 A | 4/1998 | Fodor et al. |
| 5,800,992 A | 9/1998 | Fodor et al. |
| 5,804,386 A | 9/1998 | Ju |
| 5,837,832 A | 11/1998 | Chee et al. |
| 5,854,033 A | 12/1998 | Lizardi |
| 5,866,337 A | 2/1999 | Schon |
| 5,871,921 A | 2/1999 | Landegren et al. |
| 5,888,737 A | 3/1999 | DuBridge et al. |
| 5,952,180 A | 9/1999 | Ju |
| 5,976,802 A | 11/1999 | Ansorge et al. |
| 5,994,068 A | 11/1999 | Guilfoyle et al. |
| 6,001,566 A | 12/1999 | Canard et al. |
| 6,004,755 A | 12/1999 | Wang |
| 6,013,445 A | 1/2000 | Albrecht et al. |
| 6,045,994 A | 4/2000 | Zabeau et al. |
| 6,077,668 A | 6/2000 | Kool |
| 6,087,095 A | 7/2000 | Rosenthal et al. |
| 6,087,101 A | 7/2000 | Gruelich et al. |
| 6,096,880 A | 8/2000 | Kool |
| 6,124,120 A | 9/2000 | Lizardi |
| 6,136,537 A | 10/2000 | Macevicz |
| 6,143,495 A | 11/2000 | Lizardi et al. |
| 6,143,527 A | 11/2000 | Pachuk et al. |
| 6,210,891 B1 | 4/2001 | Nyren et al. |
| 6,210,894 B1 | 4/2001 | Brennan |
| 6,218,124 B1 | 4/2001 | Lee |
| 6,218,152 B1 | 4/2001 | Auerbach |
| 6,221,603 B1 | 4/2001 | Mahtani |
| 6,255,469 B1 | 7/2001 | Seeman et al. |
| 6,258,539 B1 | 7/2001 | Hunkapiller et al. |
| 6,261,808 B1 | 7/2001 | Auerbach |
| 6,270,961 B1 | 8/2001 | Drmanac |
| 6,274,320 B1 | 8/2001 | Rothberg et al. |
| 6,274,351 B1 | 8/2001 | Peponnet |
| 6,284,497 B1 | 9/2001 | Sabanayagam et al. |
| 6,287,824 B1 | 9/2001 | Lizardi |
| 6,291,183 B1 | 9/2001 | Pirrung et al. |
| 6,297,006 B1 | 10/2001 | Drmanac et al. |
| 6,297,016 B1 | 10/2001 | Egholm et al. |
| 6,306,597 B1 | 10/2001 | Macevicz |
| 6,309,824 B1 | 10/2001 | Drmanac |
| 6,316,229 B1 | 11/2001 | Lizardi et al. |
| 6,329,150 B1 | 12/2001 | Lizardi et al. |
| 6,344,316 B1 | 2/2002 | Lockhart et al. |
| 6,344,329 B1 | 2/2002 | Lizardi |
| 6,346,413 B1 | 2/2002 | Fodor et al. |
| 6,355,432 B1 | 3/2002 | Fodor et al. |
| 6,401,267 B1 | 6/2002 | Drmanac |
| 6,403,311 B1 | 6/2002 | Chan |
| 6,403,320 B1 | 6/2002 | Read et al. |
| 6,413,722 B1 | 7/2002 | Arnold et al. |
| 6,432,360 B1 | 8/2002 | Church |
| 6,436,641 B1 | 8/2002 | Izmailov |
| 6,472,156 B1 | 10/2002 | Wittwer et al. |
| 6,491,871 B1 | 12/2002 | Fodor et al. |
| 6,500,620 B2 | 12/2002 | Yu et al. |
| 6,514,768 B1 | 2/2003 | Guire et al. |
| 6,534,293 B1 | 3/2003 | Barany et al. |
| 6,558,928 B1 | 5/2003 | Landegren |
| 6,573,369 B2 | 6/2003 | Henderson et al. |
| 6,576,448 B2 | 6/2003 | Weissman et al. |
| 6,589,726 B1 | 7/2003 | Butler et al. |
| 6,610,481 B2 | 8/2003 | Koch |
| 6,620,584 B1 | 9/2003 | Chee et al. |
| 6,632,609 B2 | 10/2003 | Lizardi |
| 6,653,077 B1 | 11/2003 | Brenner |
| 6,723,513 B2 | 4/2004 | Lexow |
| 6,783,943 B2 | 8/2004 | Christian et al. |
| 6,787,308 B2 | 9/2004 | Balasubramanian et al. |
| 6,812,005 B2 | 11/2004 | Fan et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,869,764 B2 | 3/2005 | Williams et al. |
| 6,890,741 B2 | 5/2005 | Fan et al. |
| 6,911,345 B2 | 6/2005 | Quake et al. |
| 6,913,884 B2 | 7/2005 | Stuelpnagel et al. |
| 6,977,153 B2 | 12/2005 | Kumar et al. |
| 6,998,228 B2 | 2/2006 | Henderson et al. |
| 7,011,945 B2 | 3/2006 | Qiao et al. |
| 7,033,754 B2 | 4/2006 | Chee et al. |
| 7,056,661 B2 | 6/2006 | Korlach et al. |
| 7,064,197 B1 | 6/2006 | Rabbani et al. |
| 7,226,734 B2 | 6/2007 | Chee et al. |
| 7,244,559 B2 | 7/2007 | Rothberg et al. |
| 7,264,929 B2 | 9/2007 | Rothberg et al. |
| 7,276,720 B2 | 10/2007 | Ulmer |
| 7,282,337 B1 | 10/2007 | Harris |
| 7,384,737 B2 | 6/2008 | Barnes |
| 7,544,473 B2 | 6/2009 | Brenner |
| 7,709,197 B2 | 5/2010 | Drmanac |
| 7,897,344 B2 | 3/2011 | Dahl et al. |
| 7,901,891 B2 | 3/2011 | Drmanac |
| 7,906,285 B2 | 3/2011 | Drmanac |
| 7,910,302 B2 | 3/2011 | Drmanac et al. |
| 7,910,304 B2 | 3/2011 | Drmanac |
| 7,910,354 B2 | 3/2011 | Drmanac et al. |
| 7,960,104 B2 | 6/2011 | Drmanac et al. |
| 8,105,771 B2 | 1/2012 | Drmanac |
| 8,133,719 B2 | 3/2012 | Drmanac et al. |
| 8,236,532 B2 | 8/2012 | Ronaghi et al. |
| 8,278,039 B2 | 10/2012 | Drmanac |
| 8,298,768 B2 | 10/2012 | Dramanac et al. |
| 8,415,099 B2 | 4/2013 | Drmanac et al. |
| 8,440,397 B2 | 5/2013 | Drmanac et al. |
| 8,445,194 B2 | 5/2013 | Drmanac et al. |

(56) References Cited

U.S. PATENT DOCUMENTS

| | | |
|---|---|---|
| 8,445,196 B2 | 5/2013 | Drmanac et al. |
| 8,445,197 B2 | 5/2013 | Drmanac et al. |
| 8,518,640 B2 | 8/2013 | Drmanac et al. |
| 8,551,702 B2 | 10/2013 | Drmanac et al. |
| 8,617,811 B2 | 12/2013 | Drmanac |
| 9,115,163 B2 | 8/2015 | Ju et al. |
| 9,222,132 B2 | 12/2015 | Drmanac |
| 9,523,125 B2 | 12/2016 | Drmanac |
| 10,662,473 B2 | 5/2020 | Drmanac |
| 11,098,356 B2 | 8/2021 | Drmanac |
| 11,214,832 B2 | 1/2022 | Drmanac |
| 2002/0004204 A1 | 1/2002 | O'Keefe |
| 2002/0039738 A1 | 4/2002 | Williams et al. |
| 2002/0055100 A1 | 5/2002 | Kawashima et al. |
| 2002/0076716 A1 | 6/2002 | Sabanayagam et al. |
| 2002/0164629 A1 | 11/2002 | Quake et al. |
| 2002/0192697 A1 | 12/2002 | Izmailov |
| 2002/0197621 A1 | 12/2002 | Drmanac |
| 2003/0044781 A1 | 3/2003 | Korlach et al. |
| 2003/0068629 A1 | 4/2003 | Rothberg et al. |
| 2003/0200033 A1 | 10/2003 | Segal et al. |
| 2004/0002090 A1 | 1/2004 | Mayer et al. |
| 2004/0076998 A1 | 4/2004 | Lexow |
| 2004/0229221 A1 | 11/2004 | Schon |
| 2004/0248144 A1 | 12/2004 | Mir |
| 2004/0248161 A1 | 12/2004 | Rothberg et al. |
| 2005/0019776 A1 | 1/2005 | Callow et al. |
| 2005/0037356 A1 | 2/2005 | Gullberg et al. |
| 2005/0042649 A1 | 2/2005 | Balasubramanian et al. |
| 2005/0100893 A1 | 5/2005 | Gunderson et al. |
| 2005/0100939 A1 | 5/2005 | Namsaraev et al. |
| 2005/0149272 A1 | 7/2005 | Pe' Er et al. |
| 2005/0181394 A1 | 8/2005 | Steemers et al. |
| 2005/0191656 A1 | 9/2005 | Drmanac et al. |
| 2005/0191698 A1 | 9/2005 | Chee et al. |
| 2005/0214840 A1 | 9/2005 | Chen |
| 2005/0244863 A1 | 11/2005 | Mir |
| 2006/0012793 A1 | 1/2006 | Harris |
| 2006/0024681 A1 | 2/2006 | Smith et al. |
| 2006/0024711 A1 | 2/2006 | Lapidus et al. |
| 2006/0063264 A1 | 3/2006 | Turner et al. |
| 2006/0211010 A1 | 9/2006 | Korlach et al. |
| 2006/0223097 A1 | 10/2006 | Sapolsky et al. |
| 2007/0015182 A1 | 1/2007 | Abarzua |
| 2007/0031875 A1 | 2/2007 | Buzby |
| 2007/0037152 A1 | 2/2007 | Drmanac |
| 2007/0037197 A1 | 2/2007 | Young et al. |
| 2007/0072208 A1 | 3/2007 | Drmanac |
| 2007/0099208 A1 | 5/2007 | Drmanac et al. |
| 2007/0219367 A1 | 9/2007 | Shchepinov et al. |
| 2008/0234136 A1 | 9/2008 | Drmanac et al. |
| 2008/0318796 A1 | 12/2008 | Drmanac et al. |
| 2009/0005252 A1 | 1/2009 | Drmanac et al. |
| 2009/0005259 A1 | 1/2009 | Drmanac |
| 2009/0011416 A1 | 1/2009 | Drmanac |
| 2009/0011943 A1 | 1/2009 | Drmanac et al. |
| 2009/0036316 A1 | 2/2009 | Drmanac |
| 2009/0099041 A1 | 4/2009 | Church et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0155781 A1 | 6/2009 | Drmanac et al. |
| 2009/0263802 A1 | 10/2009 | Drmanac |
| 2009/0264299 A1 | 10/2009 | Drmanac et al. |
| 2009/0305248 A1 | 12/2009 | Lander et al. |
| 2010/0105052 A1 | 4/2010 | Drmanac et al. |
| 2011/0071053 A1 | 3/2011 | Drmanac et al. |
| 2011/0281738 A1 | 11/2011 | Drmanac et al. |
| 2012/0100534 A1 | 4/2012 | Drmanac et al. |
| 2012/0141986 A1 | 6/2012 | Kuhn et al. |
| 2014/0356865 A1 | 12/2014 | Drmanac |
| 2014/0378321 A1 | 12/2014 | Drmanac |
| 2017/0292157 A1 | 10/2017 | Drmanac |
| 2018/0346980 A1 | 12/2018 | Drmanac |
| 2020/0318183 A1 | 10/2020 | Drmanac |

FOREIGN PATENT DOCUMENTS

| | | |
|---|---|---|
| JP | 04262799 A | 9/1992 |
| JP | 04304900 A | 10/1992 |
| JP | 07244046 A | 9/1995 |
| WO | 9106678 A1 | 5/1991 |
| WO | 9509248 A1 | 4/1995 |
| WO | 9844151 A1 | 10/1998 |
| WO | 0109384 A2 | 2/2001 |
| WO | 0162982 A2 | 8/2001 |
| WO | 02074988 A2 | 9/2002 |
| WO | 03012119 A2 | 2/2003 |
| WO | 2004018493 A1 | 3/2004 |
| WO | 2004018497 A2 | 3/2004 |
| WO | 2004018497 A3 | 6/2004 |
| WO | 2004072294 A2 | 8/2004 |
| WO | 2004076683 A2 | 9/2004 |
| WO | 2005024010 A1 | 3/2005 |
| WO | 2005040425 A2 | 5/2005 |
| WO | 2005047523 A2 | 5/2005 |
| WO | 2005078130 A1 | 8/2005 |
| WO | 2005080605 A2 | 9/2005 |
| WO | 2005082098 A2 | 9/2005 |
| WO | 2005093094 A2 | 10/2005 |
| WO | 2005116262 A1 | 12/2005 |
| WO | 2006002207 A2 | 1/2006 |
| WO | 2006040549 A2 | 4/2006 |
| WO | 2006055521 A2 | 5/2006 |
| WO | 2006064199 A1 | 6/2006 |
| WO | 2006073504 A2 | 7/2006 |
| WO | 2006084132 A2 | 8/2006 |
| WO | 2006120433 A1 | 11/2006 |
| WO | 2006138257 A2 | 12/2006 |
| WO | 2007014397 A2 | 2/2007 |
| WO | 2007025124 A1 | 3/2007 |
| WO | 2007061425 A1 | 5/2007 |
| WO | 2007062160 A2 | 5/2007 |
| WO | 2007010251 A3 | 8/2007 |
| WO | 2007106509 A2 | 9/2007 |
| WO | 2007120208 A2 | 10/2007 |
| WO | 2007121489 A2 | 10/2007 |
| WO | 2007123744 A2 | 11/2007 |
| WO | 2007133831 A2 | 11/2007 |
| WO | 2007146996 A2 | 12/2007 |
| WO | 2007135368 A3 | 3/2008 |

OTHER PUBLICATIONS

International Application No. PCT/US2009/032303, International Preliminary Report on Patentability mailed On Aug. 12, 2010, 8 pages.

Abi Prism® BigDye™ Terminator Cycle Sequencing Kits, Applied Biosystem, Product Bulletin, Automated DNA Sequencing, 2000, 4 pages.

Illumina Exhibit 25, US 2006/0063264 ("Turner I"), 22 pages.

Illumina Exhibit B-25, US 2006/0063264 ("Turner I"), 16 pages.

Illumina Supplemental Exhibit 23, U.S. Pat. No. 7,226,734 ("Chee III"), 70 pages.

Illumina Supplemental Exhibit B-23, U.S. Pat. No. 7,226,734 ("Chee III"), 52 pages.

Base Pair, Wikipedia, Available Online at: https://en.wikipedia.org/wiki/Base_pair#:~:text=A%20base%20pair%20(bp)%20is,of%20both%20DNA%20and%20RNA., Jun. 7, 2021, pp. 1-7.

*Complete Genomics, Inc.* v. *Illumina, Inc.*, Case No. 1:19-cv-00970-MN, Memorandum Order (re Claim Construction of U.S. Pat. Nos. 9,222,132 and 10,662,473), Feb. 16, 2021, pp. 1-14.

Defendant Illumina Inc.'s Initial Invalidity Contentions, Complete Genomics Inc. V Ilumina Inc. C.A. No. 19-970-MN, Apr. 29, 2020, 33 pages.

DNA Sequencing with Solexa Technology, Illumina's Systems & Software Technology Spotlight, 2007, 4 pages.

Fluorescent Dyes for Bioanalytical and Hightech Applications, Dyomics Colours for Life, 4th Ed, 2005, 74 pages.

Fluorophore, Wikipedia, Available Online at: https://en.wikipedia.org/wiki/Fluorophore, May 28, 2021, 11 pages.

(56) References Cited

OTHER PUBLICATIONS

Genome Analyzer Data Analysis Software, Illumina, 2008, 2 Pages.
IPR2020-00079, Illumina Incorporated v. Complete Genomics Incorporated, Paper 2, Oct. 21, 2019, 100 pages.
IPR2020-00079, Illumina, Incorporated, Complete Genomics, Incorporated., Decision Denying Institution of Inter Partes Review, Apr. 22, 2020, 46 pages.
Joint Claim Construction Brief Re: U.S. Pat. Nos. 9,222,132 and 10,662,473, *Complete Genomics Inc.* v *Ilumina Inc.* C.A. No. 19-970-MN, Nov. 25, 2020, 88 Pages.
Illumina Invalidity Contentions Exhibit B-10, US 2005/0181394 (Steemers), Jul. 31, 2020, 32 pages.
Illumina Invalidity Contentions Exhibit 01, WO 2006/064199 (Fedurco), Apr. 29, 2020, 6 pages.
Illumina Invalidity Contentions Exhibit 02, U.S. Pat. No. 6,833,246 ("Balasubramanian"), Apr. 29, 2020, 6 pages.
Illumina Invalidity Contentions Exhibit 03, WO 2004/018493 (Milton I), Apr. 29, 2020, 6 pages.
Illumina Invalidity Contentions Exhibit 04, WO 2004/018497 (Milton II), Apr. 29, 2020, 6 pages.
Illumina Invalidity Contentions Exhibit 05, U.S. 2005/0191698 (Chee I), Apr. 29, 2020, 6 pages.
Illumina Invalidity Contentions Exhibit 06, WO 2007/123744 (Banerjee), Apr. 29, 2020, 6 pages.
Illumina Invalidity Contentions Exhibit 07, Solexa Genome Analyzer, Apr. 29, 2020, 6 pages.
Illumina Invalidity Contentions Exhibit 08, U.S. Pat. No. 5,436,130 (Mathies I), Apr. 29, 2020, 6 pages.
Illumina Invalidity Contentions Exhibit 09, U.S. Pat. No. 6,403,301 (Chan), Apr. 29, 2020, 6 pages.
Illumina Invalidity Contentions Exhibit 10, US 2005/0181394 (Steemers), Apr. 29, 2020, 6 pages.
Illumina Invalidity Contentions Exhibit 11, U.S. Pat. No. 7,033,754 (Chee II), Apr. 29, 2020, 6 pages.
Illumina Invalidity Contentions Exhibit 12, US 2005/0100893 (Gunderson), Apr. 29, 2020, 6 pages.
Illumina Invalidity Contentions Exhibit 13, US 2004/007 6998 (Lexow), Apr. 29, 2020, 6 pages.
Illumina Invalidity Contentions Exhibit 14, Analytical Chemistry Excerpt (Huang I), Apr. 29, 2020, 6 pages.
Illumina Invalidity Contentions Exhibit 15, Automated DNA Sequencing and Analysis (Huang II), Apr. 29, 2020, 6 pages.
Illumina Invalidity Contentions Exhibit 16, DNA Sequencing by Capillary Electrophoresis (Ruiz-Martinez), Apr. 29, 2020, 6 pages.
Illumina Invalidity Contentions Exhibit 17, Frontiers in DNA Sequencing ("Horn-Saban "), Apr. 29, 2020, 6 pages.
Illumina Invalidity Contentions Exhibit 18, Laser-Based Detection System (Li I), Apr. 29, 2020, 6 pages.
Illumina Invalidity Contentions Exhibit 19, PerM: efficient mapping of short sequencing reads (Chen, Y), Apr. 29, 2020, 6 pages.
Illumina Invalidity Contentions Exhibit 20, Simple two-color array-based approach (Fortina), Apr. 29, 2020, 6 pages.
Illumina Invalidity Contentions Exhibit 21, Simple Two-Color Base-Calling Schemes ("Li II"), Apr. 29, 2020, 6 pages.
Illumina Invalidity Contentions Exhibit 22, U.S 201210141986AI (Kauhn), Jul. 31, 2020, 27 pages.
Illumina Invalidity Contentions Exhibit 23, U.S. Pat. No. 7,226,734 (Chee III), Jul. 31, 2020, 25 pages.
Illumina Invalidity Contentions Exhibit 24, U.S. Pat. No. 6,218,124 (Lee III), Sep. 17, 2020, 36 pages.
Illumina Invalidity Contentions Exhibit B-1, WO 2006/064199 (Fedurco), Jul. 31, 2020, 27 pages.
Illumina Invalidity Contentions Exhibit B-11, U.S. Pat. No. 7,033,754 (Chee II), Jul. 31, 2020, 62 pages.
Illumina Invalidity Contentions Exhibit B-12, US 2005/0100893 (Gunderson), Jul. 31, 2020, 69 pages.
Illumina Invalidity Contentions Exhibit B-13, US 2004/0076998 (Lexow), Jul. 31, 2020, 41 pages.
Illumina Invalidity Contentions Exhibit B-14, Analytical Chemistry Excerpt (Huang I), Jul. 31, 2020, 26 pages.
Illumina Invalidity Contentions Exhibit B-15, Automated DNA Sequencing and Analysis (Huang II), Jul. 31, 2020, 34 pages.
Illumina Invalidity Contentions Exhibit B-16, DNA Sequencing by Capillary Electrophoresis (Ruiz-Martinez), Jul. 31, 2020, 18 pages.
Illumina Invalidity Contentions Exhibit B-17, Frontiers in DNA Sequencing (Horn-Saban), Jul. 31, 2020, 70 pages.
Illumina Invalidity Contentions Exhibit B-18, Laser-Based Detection System (Li I), Jul. 31, 2020, 31 pages.
Illumina Invalidity Contentions Exhibit B-19, PerM: efficient mapping of short sequencing reads (Chen, Y), Jul. 31, 2020, 13 pages.
Illumina Invalidity Contentions Exhibit B-2, U.S. Pat. No. 6,833,246 (Balasubramanian), Jul. 31, 2020, 25 pages.
Illumina Invalidity Contentions Exhibit B-20, Intentionally Omitted, 1 page.
Illumina Invalidity Contentions Exhibit B-21, Simple Two-Color Base-Calling Schemes, (Li II), Jul. 31, 2020, 16 pages.
Illumina Invalidity Contentions Exhibit B-22, US 2012/0141986A1, (Kuhn), Jul. 31, 2020, 34 pages.
Illumina Invalidity Contentions Exhibit B-23, U.S. Pat. No. 7,226,734, (Chee III), Jul. 31, 2020, 28 pages.
Illumina Invalidity Contentions Exhibit B-3, WO 2004/018493 (Milton I), Jul. 31, 2020, 39 pages.
Illumina Invalidity Contentions Exhibit B-4, WO 2004/018497 (Milton II), Jul. 31, 2020, 57 pages.
Illumina Invalidity Contentions Exhibit B-5, U.S. 2005/0191698 (Chee I), Jul. 31, 2020, 58 pages.
Illumina Invalidity Contentions Exhibit B-6, WO 2007/123744 (Banerjee), Jul. 31, 2020, 21 pages.
Illumina Invalidity Contentions Exhibit B-7, Solexa Genome Analyzer, Jul. 31, 2020, 7 pages.
Illumina Invalidity Contentions Exhibit B-8, U.S. Pat. No. 5,436,130 ("Mathies I "), Jul. 31, 2020, 47 pages.
Illumina Invalidity Contentions Exhibit B-9, U.S. Pat. No. 6,403,311 (Chan), Jul. 31, 2020, 84 pages.
Illumina Inc.'s Amended Initial Invalidity Contentions, *Complete Genomics Inc.* v *Ilumina Inc.* C.A. No. 19-970-MN, Jul. 31, 2020, 38 Pages.
Illumina Inc.'sSecond Amended Initial Invalidity Contentions, *Complete Genomics Inc.* v *Ilumina Inc.* C.A. No. 19-970-MN, Sep. 17, 2020, 38 Pages.
Illumina Inc.'sThird Amended Initial Invalidity Contentions, *Complete Genomics Inc.* v *Ilumina Inc.* C.A. No. 19- 970-MN, Nov. 25, 2020, 40 Pages.
Patent Owner's Preliminary Response, Case IPR2020-00079, U.S. Pat. No. 9,222,132, Jan. 29, 2020, 1 page.
Table of Fluorochromes, Available Online At: http://biotech.iastate.edu/facilities/flow/Fiuorochromes.pdf, Jun. 7, 2018, pp. 1-6.
Two Dye SBS Technical Review, Illumina, Apr. 12, 2011, 52 pages.
U.S. Appl. No. 60/690,771, Methods and Applications for Random DNA Array Preparation filed Jun. 15, 2005, 35 pages.
U.S. Appl. No. 60/725,116, Ultra-High Capacity Self-Assembled Detector Nano- Array (SADNA) Chips filed Oct. 7, 2005, 45 pages.
U.S. Appl. No. 60/776,415, Efficent Genome Analysis by Combinatorial Probe Ligation on DNA Arrays filed Feb. 24, 2006, 63 pages.
Aksyonov et al., Multiplexed DNA Sequencing-by-Synthesis, Analytical Biochemistry, vol. 348, No. 1, Jan. 1, 2006, pp. 127-138.
Alberts et al., Molecular Biology of the Cell, Third Edition, 1994, 34 pages.
Bay et al., Accuracy of Two-color Peak-height-encoded DNA Sequencing by Capillary Gel Electrophoresis and Laser-induced Fluorescence, Advances in DNA Sequencing Technology Proceedings of SPIE, vol. 1891, Jun. 24, 1993, 5 pages.
Bentley, Whole-Genome Re-Sequencing, Current Opinion in Genetics & Development, vol. 16, No. 6, Dec. 2006, pp. 545-552.
Blanco et al., Highly Efficient DNA Synthesis by the Phage Phi 29 DNA Polymerase, The Journal Biological Chemistry, vol. 264, No. 15, May 25, 1989, pp. 8935-8940.
Braslavsky et al., Sequence Information Can be Obtained from Single DNA Molecules, Proceedings of National Academy of Science USA, vol. 100, No. 7, Apr. 1, 2003, pp. 3960-3964.
Brenner et al., Gene Expression Analysis by Massively Parallel Signature Sequencing (MPSS) on Microbead Arrays, Nature Biotechnology, vol. 18, No. 6, Jun. 2000, pp. 630-634.

(56) References Cited

OTHER PUBLICATIONS

Callow et al., Selective DNA Amplification from Complex Genomes Using Universal Double-Sided Adapters, Nucleic Acids Research, vol. 32, No. 2, Jan. 28, 2004, pp. 1-6.
Canard et al., DNA Polymerase Fluorescent Substrates With Reversible 3'-Tags, Gene, vol. 148, No. 1, Oct. 11, 1994, pp. 1-6.
Chen et al., A Homogeneous, Ligase-Mediated DNA Diagnostic Test, Genome Research, vol. 8, No. 5, May 1998, pp. 549-556.
Chen et al., PerM: Efficient Mapping of Short Sequencing Reads with Periodic Full Sensitive Spaced Seeds, Bioinformatics, vol. 25, No. 19, Sep. 2009, 10 pages.
Chen et al., Single-color Laser-Induced Fluorescence Detection and Capillary Gel Electrophoresis for DNA Sequencing, SPIE, vol. 1435, Jul. 1, 1991, 7 pages.
Chen et al., Two-label Peak-height Encoded DNA Sequencing by Capillary Gel Electrophoresis: Three Examples, Nucleic Acids Research, vol. 20, No. 18, Sep. 25, 1992, pp. 4873-4880.
Collins et al., Directional Cloning of DNA Fragments at a Large Distance from an Initial Probe: A Circularization Method, Proceedings of the National Academy of Sciences USA, vol. 81, No. 21, Nov. 1984, pp. 6812-6816.
Cowie et al., Identification of APC Gene Mutations in Colorectal Cancer Using Universal Microarray-Based Combinatorial Sequencing-By-Hybridization, Human Mutation, vol. 24, No. 3, Sep. 2004, pp. 261-271.
Dahl et al., Multiplex Amplification Enabled by Selective Circularization of Large Sets of Genomic DNA Fragments, Nucleic Acids Research, vol. 33, No. 8, Apr. 28, 2005, pp. 1-7.
Dorre et al., Techniques for Single Molecule Sequencing, Bioimaging, vol. 5, 1997, pp. 139-152.
Dovichi et al., How Capillary Electrophoresis Sequenced the Human Genome, Angewandte Chemie International Edition: vol. 39, No. 24, Dec. 15, 2000, pp. 4463-4468.
Drmanac et al., Sequencing by Hybridization (SBH): Advantages Achievements and Opportunities, Advances in Biochemical Engineering Biotechnology, vol. 77, Jun. 2001, pp. 75-101.
European Application No. EP12766838.2, Notice of Opposition mailed on Apr. 12, 2018, 34 pages.
European Application No. EP12766838.2, Response by Patent Owner in Opposition mailed on Sep. 5, 2018, 145 pages.
Epstein et al., Combinatorial Decoding: An Approach for Universal DNA Array Fabrication, Journal of the American Chemical Society, vol. 125, No. 45, Jun. 7, 2003, pp. 13753-13759.
Feng, Re: Evolve SDFs, Sep. 29, 2007, 3 pages.
Foldes-Papp et al., Fluorescent High-density Labeling of DNA: Error-free Substitution for a Normal Nucleotide, Journal of Biotechnology, vol. 86, Aug. 27, 1999, pp. 237-253.
Foldes-Papp et al., Fluorescently Labeled Model DNA Sequences for Exonucleolytic Sequencing, Journal of Biotechnology, vol. 86, No. 3, Apr. 13, 2001, pp. 203-224.
Fortina et al., Simple Two-color Array-based Approach for Mutation Detection, European Journal of Human Genetics, vol. 8, Oct. 31, 2000, pp. 884-894.
Fuller et al., Chapter 46 Basic DNA and RNA Protocols Methods in Molecular Biology, vol. 58, 1996, pp. 373-387.
Fung et al., High-speed DNA Sequencing by Using Mixed Poly (Ethylene Oxide) Solutions in Uncoated Capillary Columns Analytical Chemistry, vol. 67, No. 13, Jul. 1, 1995, pp. 1913-1919.
Griffin et al., Chapter 14 Methods in Molecular Biology, DNA Sequencing Protocols, vol. 23, 1993, 9 pages.
Haugland, Handbook of Fluorescent Probes and Research Products, Molecular Probes 9th Edition, 2002, 22 pages.
Hom-Saban et al., Frontiers in DNA Sequencing: the (R) Evolution of Sequencing Technologies, Encyclopedia of Analytical Chemistry: Applications Theory and Instrumentation, Dec. 2011, pp. 1-30.
Huang et al., Application of Capillary Array Electrophoresis to DNA Sequencing, Automated DNA sequencing and Analysis, Chapter 3, 1994, pp. 17-28.
Huang et al., DNA Sequencing Using Capillary Array Electrophoresis, Analytical Chemistry, vol. 64, No. 18, Sep. 15, 1992, pp. 2149-2154.
Jarvie, Next Generation Sequencing Technologies, Science Direct, Drug Discovery Today: Technologies, vol. 2, No. 3, 2005, pp. 255-260.
Ju et al., Four-color DNA Sequencing by Synthesis Using Cleavable Fluorescent Nucleotide Reversible Terminators, Proceedings of the National Academy Science USA, vol. 103, No. 52, Dec. 26, 2006, pp. 19635-19640.
Kain, 2 Dye Sequencing, Mar. 29, 2007, 1 page.
Kambara et al., Real Time Automated Simultaneous Doublestranded DNA Sequencing Using Two-Color Fluorophore Labeling, Biotechnology, vol. 9, Jul. 1991, pp. 648-651.
Kartalov et al., Microfluidic Device Reads Up to Four Consecutive Base Pairs in DNA Sequencing-by-Synthesis, Nucleic Acids Research, vol. 32, No. 9, May 20, 2004, pp. 2873-2879.
Kheterpal et al., New Methods for DNA Analysis Using Capillary Electrophoresis and Laser-Induced Fluorescence Detection, University of California Berkeley, 1998, 212 pages.
Ladner et al., Multiplex Detection of Hotspot Mutations by Rolling Circle-Enabled Universal Microarrays, Laboratory Investigation, vol. 81, No. 8, Aug. 1, 2001, pp. 1079-1086.
Lee et al., New Energy Transfer Dyes for DNA Sequencing, Nucleic Acids Research, vol. 25, No. 14, Jul. 15, 1997, pp. 2816-2822.
Li et al., Beaming Up for Detection and Quantification of Rare Sequence Variants, Nature Methods, vol. 3, No. 2, Feb. 2006, pp. 95-97.
Li et al., Laser-based Detection System for High-throughput DNA Sequencing with Multiplexed Capillary Electrophoresis, Iowa State University, 1995, 303 pages.
Li et al., Simple Two-Color Base-Calling Schemes for DNA Sequencing Based on Standard Four-Label Sanger Chemistry, Applied Spectroscopy, vol. 49, No. 10, Oct. 1, 1995, pp. 1528-1533.
Lu et al., High-Speed and High-Accuracy DNA Sequencing by Capillary Gel Electrophoresis in a Simple, Low Cost Instrument. Two-Color Peak-Height Encoded Sequencing at 40 Degrees C, Journal of Chromatography A, vol. 680, No. 2, Oct. 7, 1994, pp. 497-501.
Margulies et al., Genome Sequencing in Microfabricated High-Density Picolitre Reactors, Nature, vol. 437, No. 7057, Sep. 15, 2005, pp. 376-380.
Metzker, Emerging Technologies in DNA Sequencing, Genome Research, vol. 15, Issue 12, Dec. 2005, pp. 1767-1776.
Metzker, Sequencing Technologies—The Next Generation, Nature Reviews Genetics, vol. 11, Jan. 2010, pp. 31-46.
Metzker et al., Termination of DNA Synthesis by Novel 3'-Modifieddeoxyribonucleoside 5'-Triphosphates, Nucleic Acids Research, vol. 22, No. 20, Oct. 11, 1994, pp. 4259-4267.
Nunnally et al., Characterization of Visible Dyes for Four-Decay Fluorescence Detection in DNA Sequencing, Analytical Chemistry, vol. 69, No. 13, Jul. 1, 1997, pp. 2392-2397.
International Application No. PCT/US2009/032303, International Search Report and Written Opinion mailed on Jul. 29, 2009, 10 pages.
Prober et al., A System for Rapid DNA Sequencing with Fluorescent Chain-Terminating Dideoxynucleotides, Science, vol. 238, Oct. 16, 1987, pp. 336-341.
Quesada et al., High-sensitivity DNA Detection with a Laser-Excited Confocal Fluorescence Gel Scanner, Biotechniques, vol. 10, No. 5, Apr. 30, 1991, pp. 616-625.
Ronaghi, Pyrosequencing sheds light on DNA sequencing., Genome Research, vol. 11, No. 1, Jan. 2001, pp. 3-11.
Ronaghi et al., Real-Time DNA Sequencing Using Detection of Pyrophosphate Release, Analytical Biochemistry, vol. 242, Nov. 1996, pp. 84-89.
Rosenthal, DNA Sequencing by Chemical Degradation Using One, Two and Four Different Fluorophores, DNA Sequencing Protocols, Methods in Molecular Biology, vol. 23, 1993, pp. 261-280.
Ruiz-Martinez et al., DNA Sequencing by Capillary Electrophoresis with Replaceable Linear Polyacrylamide and Laser-induced Fluorescence Detection, Analytical Chemistry, vol. 65, No. 20, Oct. 15, 1993, pp. 2851-2858.

(56) References Cited

OTHER PUBLICATIONS

Ruparel et al., Design and Synthesis of A 3'-O-Allyl Photocleavable Fluorescent Nucleotide as a Reversible Terminator for DNA Sequencing by Synthesis, Proceedings of the National Academy of Sciences, vol. 102, No. 17, Apr. 26, 2005, pp. 5932-5937.
Sanger et al., DNA Sequencing with Chain-Terminating Inhibitors, Proceedings of the National Academy of Sciences, vol. 74, No. 12, Dec. 1977, pp. 5463-5467.
Sauer et al., Detection and Identification of Single Dye Labeled Mononucleotide Molecules Released from an Optical Fiber in a Microcapillary: First Steps Towards a New Single Molecule DNA Sequencing Technique, Physical Chemistry Chemical Physics, vol. 1, Mar. 23, 1999, pp. 2471-2477.
Shendure et al., Accurate Multiplex Polony Sequencing of an Evolved Bacterial Genome, Science, vol. 309, No. 5741, Sep. 9, 2005, pp. 1728-1732.
Shendure et al., Advanced Sequencing Technologies: Methods and Goals, Nature Reviews Genetics, vol. 5, No. 5, May 2004, pp. 335-344.
Smirnov et al., Method for Manufacturing Whole-Genome Microarrays by Rolling Circle Amplification, Genes, Chromosomes & Cancer, vol. 40, No. 1, May 2004, pp. 72-77.
Smith et al., Fluorescence detection in automated DNA sequence analysis, Nature, vol. 321, 1986, pp. 674-679.
Smith et al., Using Quality Scores and Longer Reads Improves Accuracy of Solexa Read Mapping, BMC Bioinformatics, vol. 9, No. 128, Feb. 28, 2008, pp. 1-8.
Staden, Computer Methods to Locate Signals in Nucleic Acid Sequences, Nucleic Acids Research, vol. 12, No. 1, Jan. 11, 1984, pp. 505-519.
Starke, Capillary Gel Electrophoresis for DNA Sequencing, University of Alberta, 1994, 202 pages.
Starke et al., Internal Fluorescence Labeling with Fluorescent Deoxynucleotides in Two-label Peak-height Encoded DNA Sequencing by Capillary Electrophoresis, Nucleic Acids Research, vol. 22, No. 19, Sep. 25, 1994, pp. 3997-4001.
Tabor et al., DNA Sequence Analysis with a Modified Bacteriophage T7 DNA Polymerase, The Journal of Biological Chemistry, vol. 265, No. 14, May 15, 1990, pp. 8322-8328.
Tringe et al., Metagenomics: DNA Sequencing of Environmental Samples, Nature Reviews Genetics, vol. 6, No. 11, Nov. 2005, pp. 805-814.
Vingron et al., Sequence Alignment and Penalty Choice. Review of Concepts, Case Studies and Implications, Journal of Molecular Biology, vol. 235, No. 1, Jan. 7, 1994, pp. 1-12.
Voss et al., Efficient Low Redundancy Large-Scale DNA Sequencing at EMBL, Journal of Biotechnology, vol. 41, No. 2, Jul. 31, 1995, pp. 121-129.
Watson et al., Genetical Implications of the Structure of Deoxyribonucleic Acid, Nature, vol. 171, May 30, 1953, pp. 964-967.
Whiteford et al., An Analysis of the Feasibility of Short Read Sequencing, Nucleic Acids Research, vol. 33, No. 19, Nov. 7, 2005, pp. 1-6.
Wiemann et al., Doublex Fluorescent DNA Sequencing: Two Independent Sequences Obtained Simultaneously in One Reaction with Internal Labeling and Unlabeled Primers, Analytical Biochemistry, vol. 234, No. 2, Feb. 1996, pp. 166-174.
Wiemann et al., Simultaneous on-line DNA Sequencing on Both Strands with Two Fluorescent Dyes, Analytical Biochemistry, vol. 224, No. 1, Jan. 1, 1995, pp. 117-121.
Wu et al., Termination of DNA Synthesis by N6-Alkylated not 3'-0-Alkylated Photocleavable 2'-Deoxyadenosine Triphosphates, Nucleic Acids Research, vol. 35, No. 19, Sep. 18, 2007, pp. 6339-6349.
Xue et al., High-throughput Analysis With 96-capillary Array Electrophoresis and Integrated Sample Preparation for DNA Sequencing Based on Laser Induced Fluorescence Detection, Iowa State University, 2001, 141 pages.

Xue et al., Two-color Excitation System for Fluorescence Detection in DNA Sequencing by Capillary Array Electrophoresis, Electrophoresis, vol. 23, No. 10, May 2002, pp. 1490-1498.
U.S. Appl. No. 11/938,096, Final Office Action mailed on Mar. 29, 2011, 11 pages.
U.S. Appl. No. 11/938,106, Final Office Action mailed on Dec. 1, 2011, 7 pages.
U.S. Appl. No. 11/938,106, Non-Final Office Action mailed on Apr. 12, 2011, 9 pages.
U.S. Appl. No. 11/938,106, Response to Non-Final Office Action mailed on Apr. 11, 2011, 22 pages.
U.S. Appl. No. 11/938,221, Non-Final Office Action mailed on Apr. 2, 2014, 10 pages.
U.S. Appl. No. 11/938,221, Non-Final Office Action mailed on Dec. 20, 2011, 13 pages.
U.S. Appl. No. 12/325,922, Final Office Action mailed on Dec. 21, 2011, 14 pages.
U.S. Appl. No. 12/325,922, Notice of Allowance mailed on Jun. 26, 2012, 10 pages.
U.S. Appl. No. 12/329,365, Non-Final Office Action mailed on Mar. 30, 2011, 11 pages.
U.S. Appl. No. 12/329,365, Notice of Allowability mailed on Jul. 10, 2012, 5 pages.
U.S. Appl. No. 12/329,365, Notice of Allowability mailed on Nov. 7, 2012, 5 pages.
U.S. Appl. No. 12/329,365, Notice of Allowance mailed on Jan. 20, 2012, 7 pages.
U.S. Appl. No. 12/335,188, Final Office Action mailed on Feb. 10, 2012, 23 pages.
U.S. Appl. No. 12/335,188, Non-Final Office Action mailed on May 25, 2011, 12 pages.
U.S. Appl. No. 12/361,507, Final Office Action mailed on Jan. 11, 2012, 10 pages.
U.S. Appl. No. 12/361,507, Non-Final Office Action mailed on May 12, 2011, 10 pages.
U.S. Appl. No. 12/361,507, Notice of Allowance mailed on Aug. 20, 2013, 19 pages.
U.S. Appl. No. 12/361,507, Restriction Requirement mailed on Jan. 25, 2011, 5 pages.
U.S. Appl. No. 12/573,697, Final Office Action mailed on Oct. 25, 2012, 10 pages.
U.S. Appl. No. 12/573,697, Non-Final Office Action mailed on Jan. 19, 2012, 8 pages.
U.S. Appl. No. 12/573,697, Notice of Allowance mailed on May 2, 2013, 8 pages.
U.S. Appl. No. 14/094,630, Final Office Action mailed on Jan. 25, 2016, 10 pages.
U.S. Appl. No. 14/094,630, Non-Final Office Action mailed on May 15, 2015, 8 pages.
U.S. Appl. No. 14/094,630, Notice of Allowance mailed on Oct. 6, 2016, 10 pages.
U.S. Appl. No. 14/468,213, Applicant-Initiated Interview Summary mailed on Feb. 20, 2015, 2 pages.
U.S. Appl. No. 14/468,213, Non-Final Office Action mailed on Feb. 20, 2015, 11 pages.
U.S. Appl. No. 14/468,213, Notice of Allowance mailed on Sep. 15, 2015, 8 pages.
U.S. Appl. No. 14/468,213, Restriction Requirement mailed on Dec. 19, 2014, 10 pages.
U.S. Appl. No. 15/359,277, Corrected Notice of Allowability mailed on Sep. 13, 2021, 7 pages.
U.S. Appl. No. 15/359,277, Final Office Action mailed on Jun. 12, 2019, 16 pages.
U.S. Appl. No. 15/359,277, Non-Final Office Action mailed on Oct. 4, 2018, 12 pages.
U.S. Appl. No. 15/359,277, Non-Final Office Action mailed on Oct. 5, 2020, 15 pages.
U.S. Appl. No. 15/359,277, Notice of Allowance mailed on Aug. 6, 2021, 10 pages.
U.S. Appl. No. 15/359,277, Restriction Requirement mailed on Jul. 16, 2018, 5 pages.
U.S. Appl. No. 16/054,968, Advisory Action mailed on Aug. 19, 2019, 5 pages.

(56) References Cited

OTHER PUBLICATIONS

U.S. Appl. No. 16/054,968, Final Office Action mailed on Apr. 17, 2019, 11 pages.
U.S. Appl. No. 16/054,968, Non-Final Office Action mailed on Oct. 29, 2018, 11 pages.
U.S. Appl. No. 16/054,968, Notice of Allowance mailed on Feb. 14, 2020, 11 pages.
U.S. Appl. No. 16/416,099, Final Office Action mailed on Mar. 31, 2020, 11 pages.
U.S. Appl. No. 16/416,099, Final Office Action mailed on Feb. 12, 2021, 19 pages.
U.S. Appl. No. 16/416,099, Non-Final Office Action mailed on Oct. 6, 2020, 19 pages.
U.S. Appl. No. 16/416,099, Non-Final Office Action mailed on Nov. 27, 2019, 9 pages.
U.S. Appl. No. 16/416,099, Notice of Allowance mailed on Jun. 3, 2021, 7 pages.
U.S. Appl. No. 16/882,461, Non-Final Office Action mailed on Jun. 3, 2021, 16 pages.

Probe A   C1  
Probe C   C1+C2   ⎫  
Probe G   NC      ⎬ 202  
Probe T   C2      ⎭

5'Probe A   C1         3'Probe A   C3  
5'Probe C   C1+C2      3'Probe C   C3+C4   ⎫  
5'Probe G   NC         3'Probe G   NC      ⎬ 204  
5'Probe T   C2         3'Probe T   C4      ⎭

Fig. 2

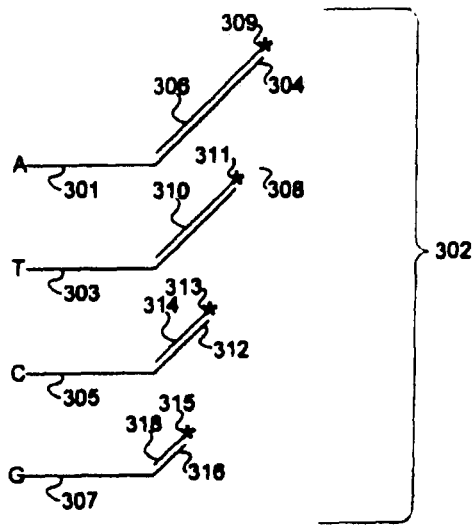

| | | | |
|---|---|---|---|
| 5'Probe Set: | 3'   5'<br>GN$_6$X$_3$<br>CN$_6$X$_5$<br>TN$_6$X$_7$<br>AN$_6$X$_9$ | 5'   3'<br>Y$_3$-C1<br>Y$_5$-C1<br>Y$_7$-C1<br>Y$_9$-C1 | |
| | 3'   5'<br>NGN$_5$X$_3$<br>NCN$_5$X$_5$<br>NTN$_5$X$_7$<br>NAN$_5$X$_9$ | 5'   3'<br>Y$_3$-C2<br>Y$_5$-C2<br>Y$_7$-C2<br>Y$_9$-C2 | |
| 3'Probe Set: | 3'   5'<br>X$_3$N$_6$G<br>X$_5$N$_6$C<br>X$_7$N$_6$T<br>X$_9$N$_6$A | 5'   3'<br>Y$_3$-C3<br>Y$_5$-C3<br>Y$_7$-C3<br>Y$_9$-C3 | |
| Fig. 3 | 3'   5'<br>X$_3$N$_5$GN<br>X$_5$N$_5$CN<br>X$_7$N$_5$TN<br>X$_9$N$_5$AN | 5'   3'<br>Y$_3$-C4<br>Y$_5$-C4<br>Y$_7$-C4<br>Y$_9$-C4 | |

Fig. 3

5'Probe Set: $GN_6$
$CN_6$—C1
$TN_6$—C1$^+$
$AN_6$—C1$^{+2}$ $NGN_5$
$NCN_5$—C2
$NTN_5$—C2$^+$
$NAN_5$—C2$^{+2}$ 3'Probe Set: $N_6G$
C3—$N_6C$
C3$^+$—$N_6T$
C3$^{+2}$—$N_6A$ $N_5GN$
C4—$N_5CN$
C4$^+$—$N_5TN$
C4$^{+2}$—$N_5AN$

Fig. 4

First Set 622:
```
CNNNNNN—C1 + C2
ANNNNNN—C1
TNNNNNN—C2
GNNNNNN—No Color (Optional)
```

Second Set 624:
```
NCNNNNN≠C1 + C2
NANNNNN≠C1
NTNNNNN≠C2
NGNNNNN≠No Color (Optional)
```

Third Set 626:
```
C3+C4—NNNNNNC
C3—NNNNNNA
C4—NNNNNNT
No Color—NNNNNNG (Optional)
```

Fourth Set 628:
```
C3+C4≠NNNNNCN
C3≠NNNNNAN
C4≠NNNNNTN
No Color≠NNNNNGN (Optional)
```

Fifth Set 632:
```
NNCNNNN—C1 + C2
NNANNNN—C1
NNTNNNN—C2
NNGNNNN—No Color (Optional)
```

Sixth Set 634:
```
NNNCNNN≠C1 + C2
NNNANNN≠C1
NNNTNNN≠C2
NNNGNNN≠No Color (Optional)
```

Seventh Set 636:
```
C3+C4—NNNNCNN
C3—NNNNANN
C4—NNNNTNN
No Color—NNNNGNN (Optional)
```

Eighth Set 628:
```
C3+C4≠NNNCNNN
C3≠NNNANNN
C4≠NNNTNNN
No Color≠NNNGNNN (Optional)
```

Fig. 6B (A) ACTTCAGAACCGCAATGCACGATACGTCTCGGGAACGCTGAAGA (SEQ ID NO: 1)

(B) GGCTCCAGCGGCTAACGATAGTCGAGCTCGAGCAATGACGTCTCGACTCAGCAGA (SEQ ID NO: 2)

(C) ACTGCTGACGTACTGCGAGAAGCTCGAGCTCGAGCCTCGAGCCTTCGACTGGAGAC (SEQ ID NO: 3)

(D) AAGTCGGAGGCCAAGCGGTCTTAGGAAGACAAGCTCGAGCTCGAGCGATCGGGCCGTACG
TCCAACTT (SEQ ID NO: 4)

(E) GCTCGAGCTCGAGC (SEQ ID NO: 5)

ADAPTOR 1

ACTTCAGAACCGCAATGCACGATACGTCTCGGGAACGCTGAAGA (SEQ ID NO. 1)

ADAPTOR 2

GCTCCAGCGGGCTAACGATGCTCGAGCAATGACGTCTCGACTCAGCAGANN (SEQ ID NO: 7)

ADAPTOR 3

TCTCCAGTCGAAGGCGAGTCGCTCGAGCTTCTCGCAGTACGTCAGCAGTNN (SEQ ID NO: 8)

ADAPTOR 4

AGTCGGAGGCCAAGCGGTCTTAGGAAGACAAGCTCGAGCTCGGGCCGTACGTCCAACTT (SEQ ID NO: 9)

(B)

METHODS AND COMPOSITIONS FOR EFFICIENT BASE CALLING IN SEQUENCING REACTIONS

CROSS REFERENCE TO RELATED APPLICATIONS

This application is a continuation of U.S. patent application Ser. No. 15/359,277, filed Nov. 22, 2016, now U.S. Pat. No. 11,214,832, which is a continuation of U.S. patent application Ser. No. 14/094,630, filed Dec. 2, 2013, now U.S. Pat. No. 9,523,125; which is a continuation of U.S. patent application Ser. No. 12/361,507, filed Jan. 28, 2009, now U.S. Pat. No. 8,617,811. The aforementioned applications claim benefit of U.S. Provisional Application Nos. 61/024,110, filed Jan. 28, 2008, and 61/024,396, filed Jan. 29, 2008. Each of Provisional Application No. 61/024,110 and No. 61/024,396 is hereby incorporated by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92171-894001_ST25.TXT, created Jun. 9, 2014, 7,285 bytes, machine format IBM-PC, MS-Windows operating system, is hereby incorporated by reference.

BACKGROUND OF THE INVENTION

Large-scale genomic sequence analysis is a key step toward understanding a wide range of biological phenomena. The need for low-cost, high-throughput sequencing and re-sequencing has led to the development of new approaches to sequencing that employ parallel analysis of multiple nucleic acid targets simultaneously.

Conventional methods of sequencing are generally restricted to determining a few tens of nucleotides before signals become significantly degraded, thus placing a significant limit on overall sequencing efficiency. Conventional methods of sequencing are also often limited by signal-to-noise ratios that render such methods unsuitable for single-molecule sequencing.

It would be advantageous for the field if methods and compositions could be designed to increase the efficiency of sequencing reactions as well as the efficiency of assembling complete sequences from shorter read lengths.

SUMMARY OF THE INVENTION

Accordingly, the present invention provides methods and compositions for base calling in sequencing reactions.

In one aspect, the present invention provides a method of identifying a first nucleotide at a detection position of a target sequence. This method includes the step of providing a surface that includes a plurality of concatemers, and each concatemer includes a plurality of monomers, and each monomer includes: (i) a first target domain of the target sequence; (ii) a first detection position; (iii) a first adaptor adjacent to said first target domain, wherein the first adaptor comprises a first anchor site. This method further includes the step of providing a first sequencing set of sequencing probes. The first set of sequencing probes includes a first, second, third and fourth probe set. The first probe set includes: (i) a first unique label; (ii) a first probe domain complementary to the first target domain; and (iii) a first unique nucleotide at a first interrogation position. The second probe set includes: (i) a second unique label; (ii) the first probe domain; and (iii) a second unique nucleotide at the first interrogation position; The third probe set includes: (i) the first and second label; (ii) the first probe domain; and (iii) a third unique nucleotide at the first interrogation position. The fourth probe set includes: (i) the first probe domain; and (ii) a fourth unique nucleotide at the first interrogation position. In this aspect of the invention, the method further includes hybridizing an anchor probe to the first anchor site and applying the set of sequencing probes to the surface. If a sequencing probe from the sequencing set has a unique nucleotide that is complementary to the first nucleotide, that sequencing probe hybridizes to the concatemer. The method further includes the step of ligating hybridized sequencing probes to hybridized anchor probes to form ligation products and then identifying the sequencing probes of those ligation products in order to identify the first nucleotide.

In some embodiments, the present invention provides a method for determining an identity of a base at a position in a target nucleic acid comprising distinguishing four nucleotides from one another in a reaction using two labels. In some aspects, the identity of the base in the target nucleic acid is determined by sequencing-by-synthesis, sequencing by hybridization, sequencing-by-ligation or cPAL.

In some aspects, the identity of a base is determined by: (a) providing library constructs comprising target nucleic acid and at least one adaptor; (b) hybridizing anchor probes to the adaptors in the library constructs; (c) hybridizing a pool of sequencing probes to the target nucleic acid, wherein a first sequencing probe identifies a base at an interrogation position and has a first label, a second sequencing probe identifies a second base at the interrogation position and has a second label, and a third sequencing probe identifies a third base at the interrogation position and has both the first and second label or some third sequencing probes have the first label and some third sequencing probes have the second label; (d) ligating the sequencing probes to the anchor probes, wherein the sequencing probe that is complementary to the target nucleic acid at the interrogated position will ligate efficiently; and (e) determining which sequencing probe if any ligated to the anchor probe so as to determine a sequence of the target nucleic acid.

In some instances, the unligated sequencing probes are discarded after step (d). Also, in some instances, processes (b) through (e) are repeated until a desired amount of sequence of target nucleic acid is obtained. In yet other instances, the pool of sequencing probes comprises a fourth sequencing probe that identifies a fourth base at the interrogation position and has no label. For example, in some specific instances, the G probe is unlabeled or unused and the C probe is labeled with two colors, and in yet other instances, the T probe is unlabeled or unused and the A probe is labeled with two colors.

In further aspects, the identity of a base is determined by: (a) providing library constructs comprising target nucleic acid and at least one adaptor, wherein the target nucleic acid has a position to be interrogated; (b) hybridizing anchor probes to the adaptors in the library constructs; (c) hybridizing a pool of sequencing probes to the target nucleic acid, wherein a first sequencing probe identifies a first base at the interrogation position and has a first label with a first intensity, a second sequencing probe identifies a second base at the interrogation position and has a first label with a second intensity, a third sequencing probe identifies a third base at the interrogation position and has a second label with a first intensity, and a fourth sequencing probe identifies a fourth base at the interrogation position and has a second label with a second intensity; (d) ligating the sequencing probes to the anchor probes, wherein the sequencing probe that is complementary to the target nucleic acid at the interrogated position will ligate efficiently; and (e) determining which sequencing probe ligated to the anchor probe so as to determine a sequence of the target nucleic acid.

Other methods of the claimed invention provide a method for determining an identity of two bases at different positions in a target nucleic acid comprising distinguishing eight nucleotides from one another using two labels.

In one aspect, the identity of two bases at different positions is determined by: (a) providing library constructs comprising target nucleic acid and at least one adaptor, wherein the target nucleic acid has a first and a second position to be interrogated; (b) hybridizing anchor probes to the adaptors in the library constructs; (c) hybridizing a pool of sequencing probes to interrogate two positions of the target nucleic acid, the pool comprising: (i) a first sequencing probe that identifies a first base at the first interrogation position comprising a first label with a first intensity, a second sequencing probe that identifies a second base at the first interrogation position comprising a first label with a second intensity, a third sequencing probe that identifies a third base at the first interrogation position comprising a first label with a third intensity, and a fourth sequencing probe that identifies a fourth base at the first interrogation position comprising a first label with a fourth intensity, and (ii) a first sequencing probe that identifies a first base at the second interrogation position comprising a second label with a first intensity, a second base sequencing probe that identifies a second base at the second interrogation position comprising a second label with a second intensity, a third sequencing probe that identifies a third base at the second interrogation position comprising a second label with a third intensity, and an fourth sequencing probe that identifies a fourth base at the second interrogation position comprising a second label with a fourth intensity; (d) ligating the sequencing probes to the anchor probes, wherein the sequencing probe that is complementary to the target nucleic acid at the interrogated positions will ligate efficiently; and (e) determining which sequencing probe ligated to the anchor probe so as to determine a sequence of the target nucleic acid.

Other methods of the claimed invention allow determination of the identity of two bases at different positions in a target nucleic acid comprising distinguishing eight nucleotides from one another using four labels.

In certain aspects, the methods comprise: (a) providing library constructs comprising target nucleic acid and at least one adaptor; (b) hybridizing anchor probes to the adaptors in the library constructs; (c) hybridizing a pool of sequencing probes to interrogate two positions of the target nucleic acid, the pool comprising: (i) a first set of sequencing probes to interrogate a first position on the target nucleic acid comprising a first sequencing probe having a first label, a second sequencing probe having a second label, and a third sequencing probe having both the first and second labels or some third sequencing probes have the first label and some third sequencing probes have the second label; and (ii) a second set of sequencing probes to interrogate a second position in the target nucleic acid comprising a first sequencing probe having a third label, a second sequencing probe having a fourth label, and a third sequencing probe having both the third and fourth labels or some third sequencing probes have the third label and some third sequencing probes have the fourth label; (d) ligating the sequencing probes to the anchor probes, wherein the sequencing probes that are complementary to the target nucleic acid at the interrogation positions will ligate efficiently to the anchor probes; and (e) determining which sequencing probes ligated to the anchor probes so as to determine a sequence of the target nucleic acid.

In some aspects of these methods, both sets of sequencing probes ligate to the same anchor. In yet other aspects, the library constructs comprise at least one or more different adaptors and hybridization sites for at least two different anchor probes, and the 3' end of one anchor probe is used for ligation with a 5' end of the first set of sequencing probes and the 5' end of another anchor probe is used for ligation with 3' end of the second set of sequencing probes. In such a case, the first set of sequencing probes can ligate to the first anchor probe but not the second anchor probe and the second set of sequencing probes can ligate to the second anchor probe but not the first anchor probe. In some aspects, the unligated sequencing probes are discarded after step (d). Also, in some aspects, processes (b) through (e) are repeated until a desired amount of sequence of target nucleic acid is obtained. In yet other aspects, the pool of sequencing probes comprises one or more fourth sequencing probes with no label.

The claimed invention also provides a method for determining an identity of four bases at different positions in a target nucleic acid comprising distinguishing sixteen nucleotides from one another using four labels.

Some aspects of methods of the invention include (a) providing library constructs comprising target nucleic acid and at least one adaptor; (b) hybridizing anchor probes to the adaptors in the library constructs; (c) hybridizing a pool of sequencing probes to interrogate four positions of the target nucleic acid, the pool comprising: (i) a first set of sequencing probes that interrogates a first position comprising a first sequencing probe having a first label, a second sequencing probe having a second label, and a third sequencing probe having both the first and second labels or some third sequencing probes have the first label and some third sequencing probes have the second label, wherein each sequencing probe of the first set interrogates a different base at the first position; (ii) a second set of sequencing probes that interrogates a second position comprising a first sequencing probe having a first dissociable label, a second sequencing probe having a second dissociable label, and a third sequencing probe having both the first and second dissociable labels or some third sequencing probes have the first disassociable label and some third sequencing probes have the second disassociable label, wherein each sequencing probe of the second set interrogates a different base at the second position; (iii) a third set of sequencing probes that interrogates a third position comprising a first sequencing probe having a third label, a second sequencing probe having a fourth label, and a third sequencing probe having both the third and fourth labels or some third sequencing probes have the third label and some third sequencing probes have the fourth label, wherein each sequencing probe of the third set interrogates a different base at the third position; (iv) a fourth set of sequencing probes that interrogates a fourth position comprising a first sequencing probe having a third dissociable label, a second sequencing probe having a fourth dissociable label, and a third sequencing probe having both the third and fourth dissociable labels or some third sequencing probes have the third disassociable label and some third sequencing probes have the fourth disassociable label, wherein each sequencing probe of the fourth set interrogates a different base at the fourth position; (d) ligating the sequencing probes to the anchor probes, wherein the sequencing probes that are complementary to the target nucleic acid at the interrogated positions will efficiently ligate to the anchor probes; (e) detecting the labels of the sequencing probes ligated to the anchor probes so as to determine a sequence of the target nucleic acid; (f) disassociating the disassociable labels in the second and fourth sets of sequencing probes; (g) detecting the labels of the sequencing probes from the first and third sets; and (h) determining which labels were disassociated and which labels remained, so as to determine a sequence of the target nucleic acid.

In further aspects processes (b) through (h) are repeated until a desired amount of sequence of target nucleic acid is obtained. Also in some aspects, the pool of sequencing probes may comprise one or more fourth sequencing probes with no label. In various aspects of this method, the disassociable labels disassociate by virtue of varying melting temperatures, and in yet other aspect, the disassociable labels disassociate by one or more cleavage reactions.

Yet other methods for determining an identity of four bases at different positions comprise: (a) providing library constructs comprising target nucleic acid and at least one adaptor; (b) hybridizing anchor probes to the adaptors in the library constructs; (c) hybridizing a pool of sequencing probes to interrogate four positions of the target nucleic acid, the pool comprising: (i) a first set of sequencing probes that interrogates a first position of the target nucleic acid, the set comprising a first sequencing probe having a first label with a first intensity, a second sequencing probe having a first label with a second intensity, and a third sequencing probe having a first label with a third intensity, wherein each sequencing probe of the first set interrogates a different base at the first position; (ii) a second set of sequencing probes that interrogates a second position of the target nucleic acid, the set comprising a first sequencing probe having a second label with a first intensity, a second sequencing probe having a second label with a second intensity, and a third sequencing probe having a second label with a third intensity, wherein each sequencing probe of the second set interrogates a different base at the second position; (iii) a third set of sequencing probes that interrogates a third position of the target nucleic acid, the set comprising a first sequencing probe having a third label with a first intensity, a second sequencing probe having a third label with a second intensity, and a third sequencing probe having a third label with a third intensity, wherein each sequencing probe of the third set interrogates a different base at the third position; and (iv) a fourth set of sequencing probes that interrogates a fourth position of the target nucleic acid, comprising a first sequencing probe having a fourth label with a first intensity, a second sequencing probe having a fourth label with a second intensity, and a third sequencing probe having a fourth label with a third intensity, wherein each sequencing probe of the fourth set interrogates a different base at the fourth position; (d) ligating the sequencing probes to the anchor probes, wherein the sequencing probes that are complementary to the target nucleic acid at the interrogated positions will efficiently ligate to the anchor probes; (e) detecting the intensity of each label of the sequencing probes ligated to the anchor probes so as to determine a sequence of the target nucleic acid.

The present invention also provides a pool of sequencing probes to interrogate a position in a target nucleic acid, comprising a first sequencing probe having a first label, a second sequencing probe having a second label, a third sequencing probe having a first and second label on one molecule or some third sequencing probes have the first label and some third sequencing probes have the second label, wherein each probe identifies a different base at the position of a target nucleic acid. In some aspects, this pool of sequencing proves further comprises a fourth probe without a label.

In some embodiments, the present invention provides a pool of sequencing probes to interrogate a position in a target nucleic acid, comprising a first sequencing probe having a first label with a first intensity, a second sequencing probe having a first label with a second intensity, a third sequencing probe having a second label with a first intensity, and a fourth sequencing probe having a second label with a second intensity, wherein each probe identifies a different base at the position of a target nucleic acid.

Also, in some aspects there is provided a pool of sequencing probes to interrogate a position in a target nucleic acid comprising a first sequencing probe having a first disassociable label, a second sequencing probe having a second disassociable label, and a third sequencing probe having both the first and second disassociable labels, wherein each probe identifies a different base at the position of a target nucleic acid. In some variations, the labels are disassociable by varying temperatures, and in other variations, the labels are disassociable by cleavage.

The described technology provides in one aspect a method for determining a sequence of a target nucleic acid comprising: (a) providing library constructs comprising target nucleic acid and at least one adaptor; (b) hybridizing at least first and second anchor probes to the at least one adaptor in the library constructs; (c) hybridizing labeled sequencing probes to the target nucleic acid; (d) ligating the labeled sequencing probes to the anchor probes, wherein the labeled sequencing probes that are complementary to the target nucleic acid will efficiently ligate to the anchor probes; (e) detecting the labels of the ligated sequencing probes; (f) providing a first invader oligonucleotide having a sequence complementary to the ligated first anchor probe; (g) allowing the first invader oligonucleotide to disrupt hybridization between the ligated first anchor probe and the library constructs by forming a complex with the ligated first anchor probe; (h) discarding the complex; and (i) detecting the labels of the remaining ligated sequencing probes to determine a sequence of a target nucleic acid.

In some aspects, processes (b) through (i) are repeated until a desired amount of sequence of target nucleic acid is obtained. In yet other aspects, the library constructs comprise at least four different adaptors, at least four different anchor probes are hybridized to the adaptors, and at least four different invader oligonucleotides substantially complementary to the four different anchor probes are provided. Additionally, in some aspects the method further comprises determining a sequence of the target nucleic acid by subtracting the label detected in (e) from the labels detected in (i). Also, in some aspects, the invader oligonucleotide is complementary to a portion of the sequencing probe.

Additionally, in some aspects of the methods of the claimed invention, the anchor probe comprises an anchor portion complementary to a portion of the adaptor, the anchor portion of the anchor probe is flanked by a tail portion; and wherein the invader oligonucleotide has a tail portion substantially complementary to the tail portion of the anchor probe. Alternatively or in addition, the anchor probe may further comprise a degenerate portion for binding target nucleic acid. Yet in other aspects, the invader oligonucleotide comprises a loop; and in some aspects, the loop is substantially complementary to a loop of an anchor probe.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

BRIEF DESCRIPTION OF THE DRAWINGS

FIG. 2 is an illustration of exemplary embodiments of probe sets of the invention.

FIG. 3 is an illustration of exemplary embodiments of probe sets of the invention.

FIG. 4 is an illustration of exemplary embodiments of probe sets of the invention.

FIGS. 6A and 6B are schematic illustrations of an embodiment of sequencing methods of the invention (A) and exemplary probe sets of use in such an embodiment (B).

FIG. 9 provides sequences of exemplary adaptors of the invention. Sequence legend: (A) (SEQ ID NO:1); (B) (SEQ ID NO:2); (C) (SEQ ID NO:3); (D) (SEQ ID NO:4); (E) (SEQ ID NO:5).

DETAILED DESCRIPTION OF THE INVENTION

Figure 1:
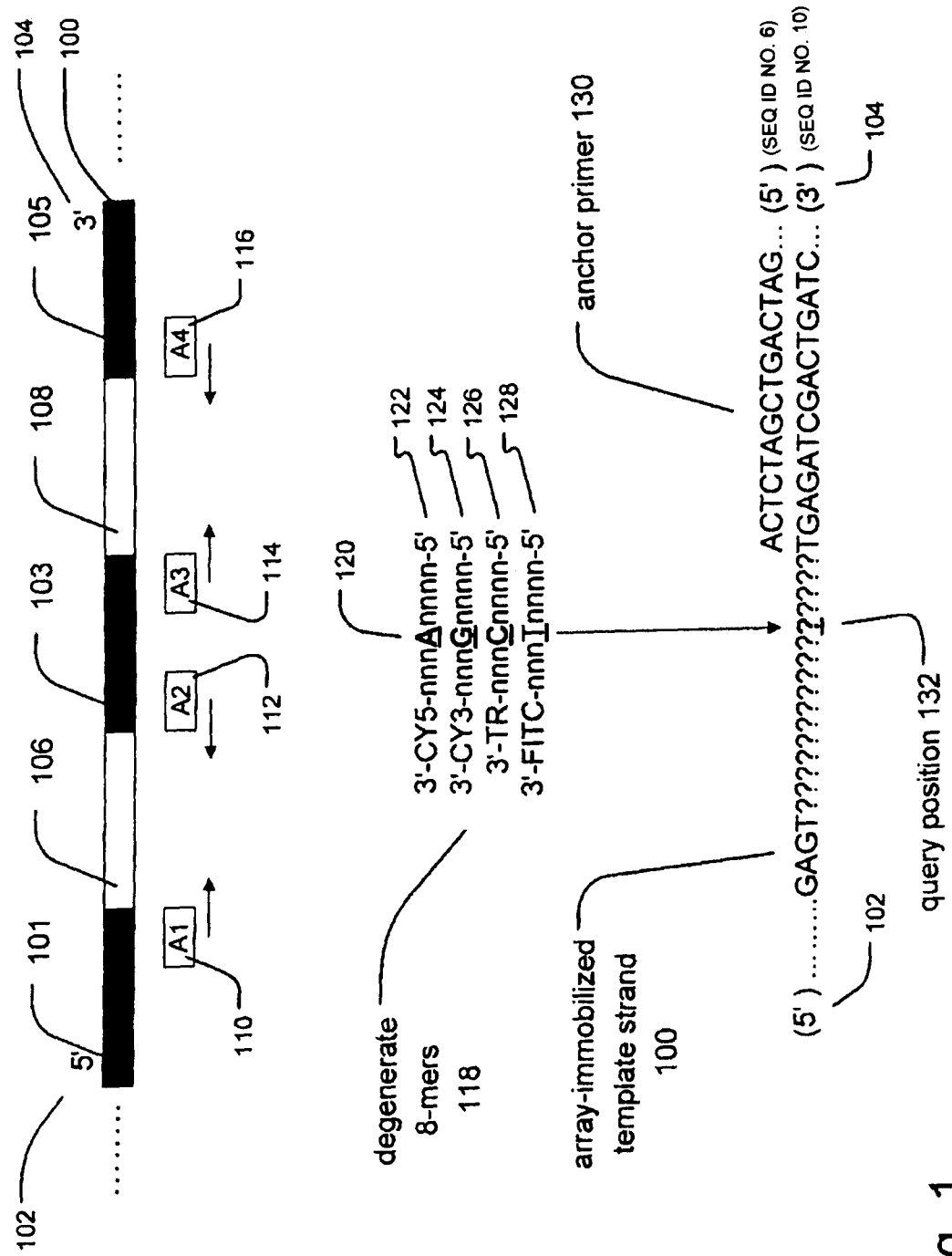
FIG. 1 is a schematic illustration of an embodiment of sequencing methods of the invention. Sequence legend: anchor primer 130 (SEQ ID NO:6); array-immobilized template strand 100 (SEQ ID NO:10).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview

The present invention is directed to methods and compositions for identifying and detecting nucleotides in a target sequence. In general, the methods are directed to new methods and improvements to technology based on the use of arrays of DNA nanoballs, sometimes referred herein as "DNBs", which can be used for extremely efficient sequencing (as well as expression analysis and genotyping). These technologies are generally described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804 (now abandoned); Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, all of which are hereby incorporated by reference in their entirety for all purposes and particularly for all disclosure related to DNBs, methods of making DNBs and methods of using DNBs. However, as will be appreciated by those in the art, the techniques described herein can be used on other platforms, e.g. other nucleic acid array systems, including both solid and liquid phase systems. Thus, while much of the description herein is directed to the discussion of DNB arrays, any and all of the techniques described herein can be applied to other platforms, in any combination.

Thus, the present invention is generally directed to the methods that allow the determination of a plurality of bases using a number of labels (e.g. fluorophores) where the number of labels is less than the number of bases that are determined at each cycle. For example, using the methods described herein, a sequencing reaction can be done in which wherein 4 bases can be distinguished using probe sets labeled with only two dyes. The ability to read two or more bases per sequencing read cycle reduces the time and cost of sequencing experiments, allowing large numbers of sequences (including whole genomes) to be detected and identified without a prohibitive increase in time and cost.

Accordingly, methods for nucleic acid identification and detection using compositions and methods of the present invention include extracting and fragmenting target nucleic acids from a sample. These fragmented nucleic acids are used to produce target nucleic acid templates that generally include one or more adaptors. The target nucleic acid templates are subjected to amplification methods to form nucleic acid concatemers, also referred to herein as nucleic acid "nanoballs" and "amplicons". In some situations, these nanoballs are disposed on a surface. Sequencing applications are performed on the nucleic acid nanoballs of the invention, usually through sequencing by ligation techniques, including combinatorial probe anchor ligation ("cPAL") methods, which are described in further detail below.

Sequencing applications of the invention will in general utilize sequencing probes that include a domain that is complementary to a domain of the target sequence as well as a unique nucleotide at an interrogation position. The methods described herein are applicable to a number of sequencing techniques, including sequencing by ligation techniques, sequencing by extension (SBE), such as described in U.S. Pat. Nos. 6,210,891; 6,828,100, 6,833,246; 6,911,345; Margulies, et al. (2005), Nature 437:376-380 and Ronaghi, et al. (1996), Anal. Biochem. 242:84-89, each of which is hereby incorporated by reference in its entirety for all purposes and in particular for all teachings related to sequencing by extension, sequencing by hybridization, such as the methods described in U.S. Pat. No. 6,401,267, which is hereby incorporated by reference in its entirety for all purposes and in particular for all teachings related to sequencing by hybridization methods. In general, these methods rely on sequencing probes that hybridize to a domain of the target nucleic acid. Such sequencing probes will in general stably hybridize to regions of the target sequence to which the sequencing probes are perfectly complementary. Conventional methods of sequencing utilize four sequencing probes that utilize four different labels to distinguish among sequencing probes for a particular nucleotide at a particular position in the target sequence—i.e., a unique label for each unique nucleotide at a specific position. (Or, alternatively, for SBE reactions, the sequencing probe is identical for each reaction but the nucleotide(s) for addition each have a unique label). The present invention provides methods and compositions that improve the efficiency and/or cost of identifying a base in a target sequence by distinguishing between the four possible nucleotides using fewer than four unique labels.

In some cases, sequencing applications of the invention use sets of sequencing probes which are labeled in such a way as to distinguish between four nucleotides using only two different labels. One example of such a set of probes is illustrated in FIG. 2. In FIG. 2, set 202 is an example of a probe set that is useful in methods where two labels are used to read four bases. As shown in 202, the A probe is labeled with a first label (identified as C1), the T probe is labeled with a second label (C2), the C probe is labeled with both the first and the second label (C1+C2), and the G probe is not labeled. In sequencing applications utilizing a probe set such as that pictured in 202, the presence of the G probe is detected when no label can be detected. The labels on probes such as those pictured in FIG. 2 can be any kind of detectable label known in the art as described more fully below, and in specific cases, fluorescent labels are used.

In some cases, sequencing applications using the nucleic acid nanoballs of the invention can detect more than two bases in a target nucleic acid by utilizing probes whose ligation to anchor probes is controlled. For example, sequencing probes can be "fixed" in orientation by blocking one end such that only sequencing probes that hybridize to a particular side of an adaptor, or in a particular orientation with respect to the anchor probe, will be able to ligate to the anchor probe. For example, in FIG. 2, set 204 is premised along the same lines as set 202, except that with set 204, four different labels are used to distinguish between 8 different nucleotides—i.e., to identify which base is present at two different locations in a target sequence. As discussed above and described in further detail below, nucleic acid nanoballs of the invention comprise repeating units of target sequence and adaptors. In specific examples of sequencing applications of the invention, four of the probes in set 204 are 3' probes, i.e., they can hybridize to locations of the target sequence 3' to an adaptor, whereas the other four probes are 5' probes and hybridize only to locations 5' to an adaptor. Similar to the labeling scheme of set 202 discussed above, the 5' probes of set 204 has an A probe labeled with a first label (C1), a T probe labeled with a second label (C2), a C probe labeled with the first and second labels (C1+C2) and a G probe that has no label. In addition, the 3' probes of set 204 has an A probe labeled with a third label (C3), a T probe labeled with a fourth label (C4), a C probe labeled with both the third and fourth label (C3+C4), and again the G probe is unlabeled. By structuring the probes in this way, a set such as probe set \*\*204 can be used to identify the nucleotide at two different positions of a target sequence.

Figure 6A:
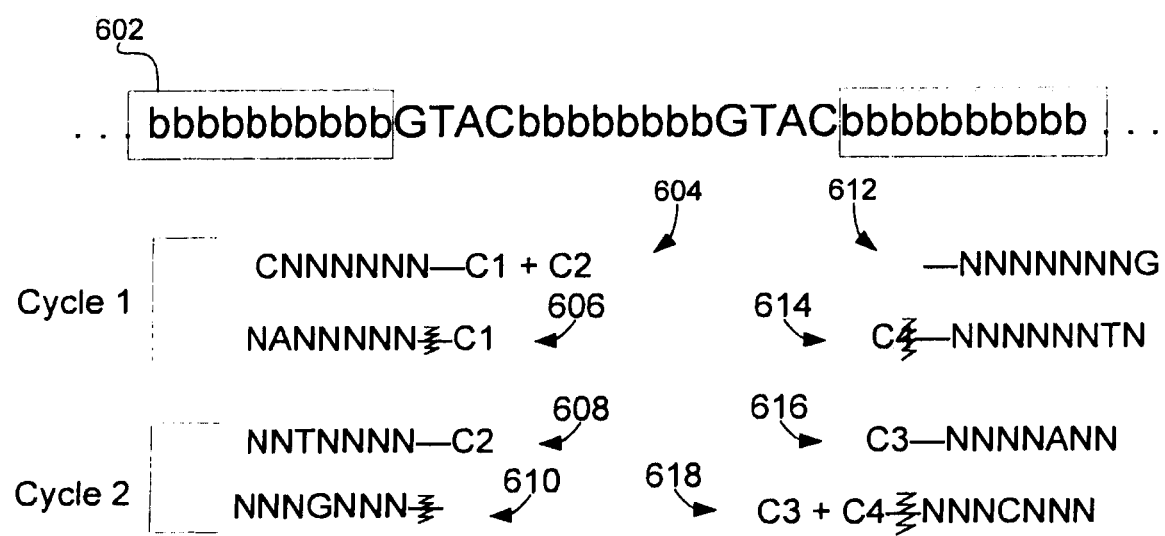

In certain cases, the nucleotides at four different positions of a target sequence in a nucleic acid nanoball are identified by using four probe sets in a single sequencing cycle to read two bases from each side of an adaptor. One example of such a sequencing application is illustrated in FIG. 6, which shows an exemplary portion of a nucleic acid nanoball 602 with adaptors on each of the 5' and 3' ends (shaded "b"s) and target nucleic acid to be sequenced in between the adaptors (i.e., in between the shaded regions). In addition, sequencing probes are shown that would allow for reading of the four bases from 5' and 3' of the two adaptors shown in two cycles. In the method of sequencing illustrated in FIG. 6, probe sets of the type shown in FIG. 2 at 204 are used; however, four probe sets are used in a single reaction to read two bases from each side. In FIG. 6, "G", "T", "A" and "C" are specific nucleotide bases, and "N"s are universal or degenerate bases. In a first cycle of sequencing, four probes sets 620 are used. A sequencing probe that would identify the G in the target nucleic acid immediately 3' to the end of the 5' adaptor is shown at 604 (CNNNNNN-C1/C2). Such a sequencing probe would be part of a first set 622: CNNNNNN-C1/C2; ANNNNNN-C1; TNNNNNN-C2 and GNNNNNN (see FIG. 6B for the probe sets that would be used in each of the two rounds of sequencing). The sequencing probe that would identify the T in the target nucleic acid two bases from the 3' end of the 5' adaptor is shown at 606 (NANNNNN‡C1), and would be part of a second set 624: NANNNNN‡C1; NTNNNNN‡C2; NGNNNNN; and NCNNNNN‡C1C2, where the symbol "‡" denotes a cleavage site). A broad variety of cleavable moieties are available in the art of solid phase and microarray oligonucleotide synthesis, including photocleavable moieties (see, e.g., Pon, R. (1993), Methods Mol. Biol. 20:465-496; Verma et al. (1998), Annu. Rev. Biochem. 67:99-134; and U.S. Pat. Nos. 5,739,386 and 5,700,642). Again, using a G probe in this instance is optional, since the G probe does not have a label.

A sequencing probe that would identify the C in the target nucleic acid immediately 5' to the end of the 3' adaptor is shown at 612 (NNNNNNG). Such a sequencing probe would be part of a third set 626: NNNNNNG; C3/C4-NNNNNC; C31-NNNNNA; and C4-NNNNNT. The sequencing probe that would identify the A in the target nucleic acid two bases from the 5' end of the 3' adaptor is shown at 614 (C4‡NNNNTN), and would be part of a fourth set 628: C4‡NNNNTN; C3‡NNNNAN; NNNNNGN; and C3C4‡NNNNCN, again, where the symbol "‡" denotes a cleavage site. The first, second, third and fourth sequencing probe sets are used together to sequence four bases at a time in the following manner: Anchor probes are allowed to hybridize to the adaptors in the library constructs after which (or simultaneously) all four sets of sequencing probes are added and allowed to hybridize to the target nucleic acid. The adjacently-hybridized anchor probes and sequencing probes may then be ligated to one another if the sequencing probe is complementary to the target nucleic acid in the library construct. An extensive wash is performed to eliminate unligated sequencing probes. Two sequencing probes will ligate to the anchor probes that hybridized to the 5' adaptor (one sequencing probe from the first sequencing probe set (604) and one sequencing probe from the second sequencing probe set (606)), and two sequencing probes will ligate to anchor probes that hybridized to the 3' adaptor (one sequencing probe from the third sequencing probe set (612) and one sequencing probe from the fourth sequencing probe set (614)). It should be noted that more than one sequencing probe will not ligate to a single anchor probe, but about half of the 5' anchor probes will ligate to sequencing probes from the first set, and about half of the 5' anchor probes will ligate to sequencing probes from the second set. Similarly, about half of the 3' anchor probes will ligate to sequencing probes from the third set, and about half of the 5' anchor probes will ligate to sequencing probes from the fourth set.

The fluorescent signal for the first read out in this hypothetical would be C1+C2+C1 from the 5' side and no color (from the G sequencing probe)+C4 from the 3' side. The sequencing reaction mix is then subjected to cleaving at the "‡" site, eliminating the fluorescent signal from the sequencing probes interrogating the bases in the target nucleic acid two nucleotides from the ligation junction (i.e., sequencing probes from the second and fourth sequencing probe sets). A wash is then performed, and the fluorescent signal is read again. The fluorescent signal for the second read out in this hypothetical would be C1+C2 from the 5' side and no color from the 3' side. That is, the strong C1 signal contributed by the NANNNNN‡CL sequencing probe (606) and the C4 signal contributed by the C2‡NNNNNTN sequencing probe (614) will have disappeared. The disappearance of a strong C1 signal indicates that a T is two bases from the 3' end of the 5' adaptor (the A sequencing probe from the second set ligated to the anchor probe). The disappearance of the C4 signal indicates that an A is two bases from the 5' end of the 3' adaptor (the T sequencing probe from the fourth set ligated to the anchor probe). The remaining C1+C2 signal indicates that a G is in the first position in the target nucleic acid immediately 3' to the end of the 5' adaptor (the C sequencing probe from the first set ligated to the anchor probe) and that there is no color at all from the third sequencing probe set indicates that a C is the first base in the target nucleic acid immediately 5' to the end of the 3' adaptor (the G sequencing probe from the third set ligated to the anchor probe).

Further examples of sequencing methods using combinations of probe sets according to the present invention are described in further detail below.

II. Nucleic Acid Nanoballs and Arrays

Compositions of the invention include nucleic acid templates, concatemers generated from such nucleic acid templates, as well as substrates comprising a surface with a plurality of such concatemers disposed on that surface (also referred to herein as "arrays"). Such compositions are described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278, 039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266, 385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329, 365, now U.S. Pat. No. 8,415,099; Ser. No. 12/335,188, now U.S. Pat. No. 8,551,702; and Ser. No. 12/359,165, now abandoned, all of which are hereby incorporated by reference in their entirety for all purposes and particularly for all disclosure related to nucleic acid templates, concatemers and arrays according to the present invention.

In one aspect, the present invention provides nucleic acid templates comprising target nucleic acids and multiple interspersed adaptors, also referred to herein as "library constructs," "circular templates", "circular constructs", "target nucleic acid templates", and other grammatical equivalents. The nucleic acid template constructs of the invention are assembled by inserting adaptors molecules at a multiplicity of sites throughout each target nucleic acid. The interspersed adaptors permit acquisition of sequence information from multiple sites in the target nucleic acid consecutively or simultaneously.

The term "target nucleic acid" refers to a nucleic acid of interest. In one aspect, target nucleic acids of the invention are genomic nucleic acids, although other target nucleic acids can be used, including mRNA (and corresponding cDNAs, etc.). Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification, isolated by amplification using methods known in the art, including without limitation polymerase chain reaction (PCR), strand displacement amplification (SDA), multiple displacement amplification (MDA), rolling circle amplification (RCA), rolling circle amplification (RCR) and other amplification (including whole genome amplification) methodologies. Target nucleic acids may also be obtained through cloning, including but not limited to cloning into vehicles such as plasmids, yeast, and bacterial artificial chromosomes.

In some aspects, the target nucleic acids comprise mRNAs or cDNAs. In certain embodiments, the target DNA is created using isolated transcripts from a biological sample. Isolated mRNA may be reverse transcribed into cDNAs using conventional techniques, again as described in Genome Analysis: A Laboratory Manual Series (Vols. I-IV) or Molecular Cloning: A Laboratory Manual.

Target nucleic acids can be obtained from a sample using methods known in the art. As will be appreciated, the sample may comprise any number of substances, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample. In one aspect, the nucleic acid constructs of the invention are formed from genomic DNA. In certain embodiments, the genomic DNA is obtained from whole blood or cell preparations from blood or cell cultures.

In an exemplary embodiment, genomic DNA is isolated from a target organism. By "target organism" is meant an organism of interest and as will be appreciated, this term encompasses any organism from which nucleic acids can be obtained, particularly from mammals, including humans, although in some embodiments, the target organism is a pathogen (for example for the detection of bacterial or viral infections). Methods of obtaining nucleic acids from target organisms are well known in the art. Samples comprising genomic DNA of humans find use in many embodiments. In some aspects such as whole genome sequencing, about 20 to about 1,000,0000 or more genome-equivalents of DNA are preferably obtained to ensure that the population of target DNA fragments sufficiently covers the entire genome. The number of genome equivalents obtained may depend in part on the methods used to further prepare fragments of the genomic DNA for use in accordance with the present invention.

The target nucleic acids used to make templates of the invention may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

By "nucleic acid" or "oligonucleotide" or "polynucleotide" or grammatical equivalents herein means at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat.

Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" (LNA™) are also included within the definition of nucleic acid analogs. LNAs are a class of nucleic acid analogues in which the ribose ring is "locked" by a methylene bridge connecting the 2'-0 atom with the 4'-C atom. All of these references are hereby expressly incorporated by reference in their entirety for all purposes and in particular for all teachings related to nucleic acids. These modifications of the ribose-phosphate backbone may be done to increase the stability and half-life of such molecules in physiological environments. For example, PNA:DNA and LNA-DNA hybrids can exhibit higher stability and thus may be used in some embodiments.

The nucleic acid templates of the invention comprise target nucleic acids and adaptors. As used herein, the term "adaptor" refers to an oligonucleotide of known sequence. Adaptors of use in the present invention may include a number of elements. The types and numbers of elements (also referred to herein as "features", "functional elements" and grammatical equivalents) included in an adaptor will depend on the intended use of the adaptor. Adaptors of use in the present invention will generally include without limitation sites for restriction endonuclease recognition and/or cutting, particularly Type IIs recognition sites that allow for endonuclease binding at a recognition site within the adaptor and cutting outside the adaptor as described below, sites for primer binding (for amplifying the nucleic acid constructs) or anchor primer (sometimes also referred to herein as "anchor probes") binding (for sequencing the target nucleic acids in the nucleic acid constructs), nickase sites, and the like. In some embodiments, adaptors will comprise a single recognition site for a restriction endonuclease, whereas in other embodiments, adaptors will comprise two or more recognition sites for one or more restriction endonucleases. As outlined herein, the recognition sites are frequently (but not exclusively) found at the termini of the adaptors, to allow cleavage of the double stranded constructs at the farthest possible position from the end of the adaptor. Adaptors of use in the invention are described herein and in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, all of which are hereby incorporated by reference in their entirety for all purposes and particularly for all disclosure related to adaptors and target nucleic acid templates comprising adaptors.

In some embodiments, adaptors of the invention have a length of about 10 to about 250 nucleotides, depending on the number and size of the features included in the adaptors. In certain embodiments, adaptors of the invention have a length of about 50 nucleotides. In further embodiments, adaptors of use in the present invention have a length of about 20 to about 225, about 30 to about 200, about 40 to about 175, about 50 to about 150, about 60 to about 125, about 70 to about 100, and about 80 to about 90 nucleotides.

In further embodiments, adaptors may optionally include elements such that they can be ligated to a target nucleic acid as two "arms". One or both of these arms may comprise an intact recognition site for a restriction endonuclease, or both arms may comprise part of a recognition site for a restriction endonuclease. In the latter case, circularization of a construct comprising a target nucleic acid bounded at each termini by an adaptor arm will reconstitute the entire recognition site.

In still further embodiments, adaptors of use in the invention will comprise different anchor binding sites (also referred to herein as "anchor sites") at their 5' and the 3' ends. As described further herein, such anchor binding sites can be used in sequencing applications, including the combinatorial probe anchor ligation (cPAL) method of sequencing, described herein and in U.S. application Ser. No. 11/679,124, now abandoned; Ser. No. 11/981,761, now U.S. Pat. No. 8,440,397; Ser. No. 11/981,661; Ser. No. 11/981,605; Ser. No. 11/981,793; Ser. No. 11/981,804; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221; Ser. No. 12/325,922, now U.S. Pat. No. 8,298,768; Ser. No. 12/329,365, now U.S. Pat. No. 8,415,099; Ser.

No. 12/335,188, now U.S. Pat. No. 8,551,702; and Ser. No. 12/359,165, now abandoned, all of which are hereby incorporated by reference in their entirety for all purposes and particularly for all disclosure related to, all of which are hereby incorporated by reference in their entirety, and particularly for all disclosure related to sequencing by ligation.

In one aspect, adaptors of the invention are interspersed adaptors. By "interspersed adaptors" is meant herein oligonucleotides that are inserted at spaced locations within the interior region of a target nucleic acid. In one aspect, "interior" in reference to a target nucleic acid means a site internal to a target nucleic acid prior to processing, such as circularization and cleavage, that may introduce sequence inversions, or like transformations, which disrupt the ordering of nucleotides within a target nucleic acid. "Interspersed adaptors" can be inserted such that they interrupt a contiguous target sequence, thus conferring a spatial and distance orientation between the target sequences. That is, as outlined herein and in the incorporated applications, using endonucleases that cut outside of the recognition sequence allows the precise insertion (via ligation) of adaptors at defined intervals within the target sequence. This facilitates sequence reconstruction and alignment, as sequence runs of 10 bases each from a single adaptor can allow 20, 30, 40, etc. bases to be read without alignment, per se.

The nucleic acid template constructs of the invention contain multiple interspersed adaptors inserted into a target nucleic acid, and in a particular orientation. As discussed further herein, the target nucleic acids are produced from nucleic acids isolated from one or more cells, including one to several million cells. These nucleic acids are then fragmented using mechanical or enzymatic methods.

The target nucleic acid that becomes part of a nucleic acid template construct of the invention may have interspersed adaptors inserted at intervals within a contiguous region of the target nucleic acids at predetermined positions. The intervals may or may not be equal. In some aspects, the accuracy of the spacing between interspersed adaptors may be known only to an accuracy of one to a few nucleotides. In other aspects, the spacing of the adaptors is known, and the orientation of each adaptor relative to other adaptors in the library constructs is known. That is, in many embodiments, the adaptors are inserted at known distances, such that the target sequence on one terminus is contiguous with the naturally occurring genomic sequence with the target sequence on the other terminus. For example, in the case of a Type IIs restriction endonuclease that cuts 16 bases from the recognition site, if the recognition site is located 3 bases into the adaptor, the endonuclease cuts 13 bases from the end of the adaptor. Upon the insertion of a second adaptor, the target sequence "upstream" of the adaptor and the target sequence "downstream" of the adaptor are actually contiguous sequences in the original target sequence. Thus, the interspersed adaptors of the present invention are truly "inserted" into a target sequence rather than simply appended to the ends of fragments randomly generated through enzymatic and mechanical methods.

Although the embodiments of the invention described herein are generally described in terms of circular nucleic acid template constructs, it will be appreciated that nucleic acid template constructs may also be linear. Furthermore, nucleic acid template constructs of the invention may be single- or double-stranded, with the latter being preferred in some embodiments.

In further embodiments, nucleic acid templates formed from a plurality of genomic fragments can be used to create a library of nucleic acid templates. Such libraries of nucleic acid templates will in some embodiments encompass target nucleic acids that together encompass all or part of an entire genome. That is, by using a sufficient number of starting genomes (e.g. cells), combined with random fragmentation, the resulting target nucleic acids of a particular size that are used to create the circular templates of the invention sufficiently "cover" the genome, although as will be appreciated, on occasion, bias may be introduced inadvertently to prevent the entire genome from being represented.

The nucleic acid template constructs of the invention comprise multiple interspersed adaptors, and in some aspects, these interspersed adaptors comprise one or more recognition sites for restriction endonucleases. In further aspect, the adaptors comprise recognition sites for Type IIs endonucleases. Type-IIs endonucleases are generally commercially available and are well known in the art. Like their Type-II counterparts, Type-IIs endonucleases recognize specific sequences of nucleotide base pairs within a double stranded polynucleotide sequence. Upon recognizing that sequence, the endonuclease will cleave the polynucleotide sequence, generally leaving an overhang of one strand of the sequence, or "sticky end." Type-IIs endonucleases also generally cleave outside of their recognition sites; the distance may be anywhere from about 2 to 30 nucleotides away from the recognition site depending on the particular endonuclease. Some Type-IIs endonucleases are "exact cutters" that cut a known number of bases away from their recognition sites. In some embodiments, Type IIs endonucleases are used that are not "exact cutters" but rather cut within a particular range (e.g. 6 to 8 nucleotides). Generally, Type IIs restriction endonucleases of use in the present invention have cleavage sites that are separated from their recognition sites by at least six nucleotides (i.e. the number of nucleotides between the end of the recognition site and the closest cleavage point). Exemplary Type IIs restriction endonucleases include, but are not limited to, Eco57M 1, Mme 1, Acu I, Bpm I, BceA 1, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like. In some exemplary embodiments, the Type IIs restriction endonucleases used in the present invention are AcuI, which has a cut length of about 16 bases with a 2-base 3' overhang and EcoP15, which has a cut length of about 25 bases with a 2-base 5' overhang. As will be discussed further below, the inclusion of a Type IIs site in the adaptors of the nucleic acid template constructs of the invention provides a tool for inserting multiple adaptors in a target nucleic acid at a defined location.

As will be appreciated, adaptors may also comprise other elements, including recognition sites for other (non-Type IIs) restriction endonucleases, including Type I and Type III restriction endonucleases, as well as Type II endonucleases (including IIB, IIE, IIG, IIM, and any other enzymes known in the art), primer binding sites for amplification as well as binding sites for probes used in sequencing reactions ("anchor probes"), described further herein. Type III endonucleases, similar to the Type IIs endonucleases, cut at sites outside of their recognition sites. These enzymes, as for many of the enzymes recited herein, may also be used in to control the inactivation and activation of restriction endonuclease recognition sites through methylation, as described in U.S. application Ser. No. 12/265,593, now U.S. Pat. No. 7,901,890; Ser. No. 12/266,385, now U.S. Pat. No. 7,897,344; Ser. No. 12/329,365, now U.S. Pat. No. 8,415,099; and Ser. No. 12/335,188, now U.S. Pat. No. 8,551,702, each of which is herein incorporated by reference in its entirety for all purposes and in particular for all teachings related to the insertion of multiple adaptors and the control over recognition sites for restriction endonucleases contained in such adaptors.

Figure 10:
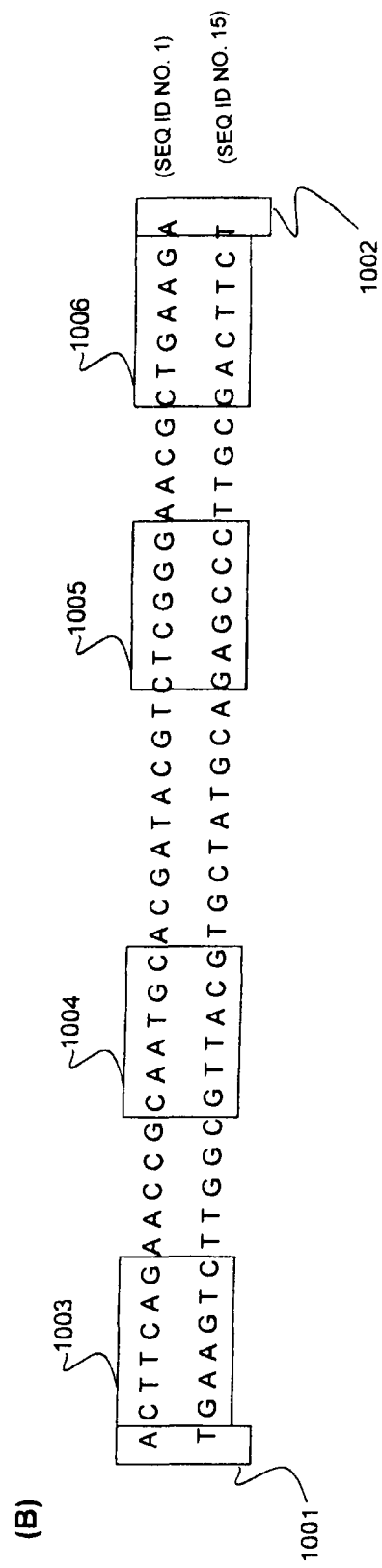
FIG. 10 provides (A) sequences of exemplary adaptors of the invention and (B) a schematic illustration of exemplary functional elements of an adaptor. Sequence legend: (A): Adaptor 1 (SEQ ID NO:1); Adaptor 2 (SEQ ID NO:7); Adaptor 3 (SEQ ID NO:8); Adaptor 4 (SEQ ID NO:9); (B) upper sequence (SEQ ID NO:1); lower sequence (SEQ ID NO:15).

In one aspect, adaptors of use in the invention have sequences as shown in FIGS. 9 and 10 (SEQ ID NOs. 1-9). In further aspects, adaptors of use in the invention may comprise one or more of the sequences illustrated in FIGS. 9 and 10. As will be appreciated, sequences that have at least 65%, 70%, 75%, 80%, 85%, 90%, 91%, 92%, 93%, 94%, 95%, 96%, 97%, 98%, and 99% sequence identity to the sequences provided in FIGS. 1 and 2 are also encompassed by the present invention. As identified in the schematic of one of the adaptors in FIG. 10B, adaptors can comprise multiple functional features, including recognition sites for Type IIs restriction endonucleases (1003 and 1006), sites for nicking endonucleases (1004) as well as sequences that can influence secondary characteristics, such as bases to disrupt hairpins (1001 and 1002).

In further embodiments, adaptors of use in the invention contain stabilizing sequences. By the term "stabilizing sequences" or "stabilization sequences" herein is meant nucleic acid sequences that facilitate DNB formation and/or stability. For example, stabilization sequences can allow the formation of secondary structures within the DNBs of the invention. Complementary sequences, including palindromic sequences, find particular use in the invention. In some cases, it is possible to use nucleic acid binding proteins and their recognition sequences as stabilization sequences, or crosslinking components as is more fully described below. Multiple configurations of stabilizing sequences can be used in the invention, and will depend in part upon the numbers of adaptors used in the constructs, the desired structures of the amplicon, and the placement of the binding region in each construct relative to the stabilizing sequences. Stabilizing sequences (also referred to as "secondary structure sequences") are described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, all of which are hereby incorporated by reference in their entirety for all purposes and particularly for all disclosure related to stabilizing and secondary structure sequences.

In some embodiments, concatemers of the invention are disposed on the surface of a substrate. Methods for making such compositions (also referred to herein as "arrays") are described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702, and Ser. No. 12/359,165, now abandoned, all of which are hereby incorporated by reference in their entirety for all purposes and particularly for all disclosure related to arrays of concatemers and methods of making such arrays.

In certain embodiments, arrays of the invention comprise concatemers that are randomly disposed on an unpatterned or patterned surface. In certain embodiments, arrays of the invention comprise concatemers that are disposed in known locations on an unpatterned or patterned surface. Arrays of the invention may comprise concatemers fixed to surface by a variety of techniques, including covalent attachment and non-covalent attachment. In one embodiment, a surface may include capture probes that form complexes, e.g., double stranded duplexes, with component of a polynucleotide molecule, such as an adaptor oligonucleotide. In other embodiments, capture probes may comprise oligonucleotide clamps, or like structures, that form triplexes with adaptors, as described in Gryaznov et al, U.S. Pat. No. 5,473,060, which is hereby incorporated in its entirety for all purposes and in particular for all teachings related to arrays.

III. Sequencing Methods

The present invention provides methods and compositions for identifying multiple bases in a target nucleic acid by utilizing sets of probes that can distinguish between four possible bases at one or more positions in a target sequence using fewer than four labels in a set of sequencing probes. The methods of the present invention allow for multiple base calls per sequencing cycle, thus reducing the time and cost of sequencing and detection of sequences of target nucleic acids.

Although the following description of sequencing applications of the present invention is provided in terms of DNBs, it will be appreciated that these methods can be applied to any nucleic acid targets and are not necessarily limited to concatemers comprising target sequence and adaptors.

Methods of using DNBs in accordance with the present invention include sequencing and detecting specific sequences in target nucleic acids (e.g., detecting particular target sequences (e.g. specific genes) and/or identifying and/or detecting SNPs). The methods described herein can also be used to detect nucleic acid rearrangements and copy number variation. Nucleic acid quantification, such as digital gene expression (i.e., analysis of an entire transcriptome—all mRNA present in a sample) and detection of the number of specific sequences or groups of sequences in a sample, can also be accomplished using the methods described herein. Methods of using DNBs in sequencing reactions and in the detection of particular target sequences are also described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, each of which is herein incorporated by reference in its entirety for all purposes and in particular for all teachings related conducting sequencing reactions on DNBs of the invention. As will be appreciated, any of the sequencing methods described herein and known in the art can be applied to nucleic acid templates and/or DNBs of the invention in solution or to nucleic acid templates and/or DNBs disposed on a surface and/or in an array.

In one aspect, sequences of DNBs are identified using sequencing methods known in the art, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, and sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003); Smith et al, PCT publication WO 2006/074351; and ligation-based methods, e.g. Shendure et al (2005), Science, 309: 1728-1739, Macevicz, U.S. Pat. No. 6,306,597, wherein each of these references is herein incorporated by reference in its entirety for all purposes and in particular teachings regarding the figures, legends and accompanying text describing the compositions, methods of using the compositions and methods of making the compositions, particularly with respect to sequencing.

In some embodiments, nucleic acid templates of the invention, as well as DNBs generated from those templates, are used in sequencing by synthesis methods. The efficiency of sequencing by synthesis methods utilizing nucleic acid templates of the invention is increased over conventional sequencing by synthesis methods utilizing nucleic acids that do not comprise multiple interspersed adaptors. Rather than a single long read, nucleic acid templates of the invention allow for multiple short reads that each start at one of the adaptors in the template. Such short reads consume fewer labeled dNTPs, thus saving on the cost of reagents. In addition, sequencing by synthesis reactions can be performed on DNB arrays, which provide a high density of sequencing targets as well as multiple copies of monomeric units. Such arrays provide detectable signals at the single molecule level while at the same time providing an increased amount of sequence information, because most or all of the DNB monomeric units will be extended without losing sequencing phase. The high density of the arrays also reduces reagent costs—in some embodiments the reduction in reagent costs can be from about 30 to about 40% over conventional sequencing by synthesis methods. In some embodiments, the interspersed adaptors of the nucleic acid templates of the invention provide a way to combine about two to about ten standard reads if inserted at distances of from about 30 to about 100 bases apart from one another. In such embodiments, the newly synthesized strands will not need to be stripped off for further sequencing cycles, thus allowing the use of a single DNB array through about 100 to about 400 sequencing by synthesis cycles.

IIIA. Sequencing by Ligation Using cPAL Methods

In one aspect, the present invention provides methods for identifying sequences of DNBs that utilize a sequencing by ligation method. In specific embodiments, the sequencing by ligation method used is a combinatorial probe anchor ligation (cPAL) method. Generally, cPAL involves identifying a nucleotide at a detection position in a target nucleic acid by detecting a probe ligation product formed by ligation of at least one anchor probe and at least one sequencing probe. Such methods are described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, each of which is herein incorporated by reference in its entirety for all purposes and in particular for all teachings related to cPAL sequencing methods. Methods of the invention can be used to sequence a portion or the entire sequence of the target nucleic acid contained in a DNB, and many DNBs that represent a portion or all of a genome.

As discussed further herein, every DNB comprises repeating monomeric units, each monomeric unit comprising one or more adaptors and a target nucleic acid. The target nucleic acid comprises a plurality of detection positions. The term "detection position" refers to a position in a target sequence for which sequence information is desired. As will be appreciated by those in the art, generally a target sequence has multiple detection positions for which sequence information is required, for example in the sequencing of complete genomes as described herein. In some cases, for example in SNP analysis, it may be desirable to just read a single SNP in a particular area.

The present invention provides methods of sequencing by ligation that utilize a combination of anchor probes and sequencing probes. By "sequencing probe" as used herein is meant an oligonucleotide that is designed to provide the identity of a nucleotide at a particular detection position of a target nucleic acid. Sequencing probes hybridize to domains within target sequences, e.g. a first sequencing probe may hybridize to a first target domain, and a second sequencing probe may hybridize to a second target domain. The terms "first target domain" and "second target domain" or grammatical equivalents herein means two portions of a target sequence within a nucleic acid which is under examination. The first target domain may be directly adjacent to the second target domain, or the first and second target domains may be separated by an intervening sequence, for example an adaptor. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. Sequencing probes can overlap, e.g. a first sequencing probe can hybridize to the first 6 bases adjacent to one terminus of an adaptor, and a second sequencing probe can hybridize to the 3rd-9th bases from the terminus of the adaptor (for example when an anchor probe has three degenerate bases). Alternatively, a first sequencing probe can hybridize to the 6 bases adjacent to the "upstream" terminus of an adaptor and a second sequencing probe can hybridize to the 6 bases adjacent to the "downstream" terminus of an adaptor.

Sequencing probes will generally comprise a number of degenerate bases and a specific nucleotide at a specific location within the probe to query the detection position (also referred to herein as an "interrogation position").

In general, pools of sequencing probes are used when degenerate bases are used. That is, a probe having the sequence "NNNANN" is actually a set of probes of having all possible combinations of the four nucleotide bases at five positions (i.e., 1024 sequences) with an adenosine at the 6th position. (As noted herein, this terminology is also applicable to adaptor probes: for example, when an adaptor probe has "three degenerate bases", for example, it is actually a set of adaptor probes comprising the sequence corresponding to the anchor site, and all possible combinations at 3 positions, so it is a pool of 64 probes).

In some embodiments, for each interrogation position, four differently labeled pools can be combined in a single pool and used in a sequencing step. Thus, in any particular sequencing step, 4 pools are used, each with a different specific base at the interrogation position and with a different label corresponding to the base at the interrogation position. That is, sequencing probes are also generally labeled such that a particular nucleotide at a particular interrogation position is associated with a label that is different from the labels of sequencing probes with a different nucleotide at the same interrogation position. For example, four pools can be used: NNNANN-dye1, NNNTNN-dye2, NNNCNN-dye3 and NNNGNN-dye4 in a single step, as long as the dyes are optically resolvable. In some embodiments, for example for SNP detection, it may only be necessary to include two pools, as the SNP call will be either a C or an A, etc. Similarly, some SNPs have three possibilities. Alternatively, in some embodiments, if the reactions are done sequentially rather than simultaneously, the same dye can be done, just in different steps: e.g. the NNNANN-dye1 probe can be used alone in a reaction, and either a signal is detected or not, and the probes washed away; then a second pool, NNNTNN-dye1 can be introduced.

In any of the sequencing methods described herein, sequencing probes may have a wide range of lengths, including about 3 to about 25 bases. In further embodiments, sequencing probes may have lengths in the range of about 5 to about 20, about 6 to about 18, about 7 to about 16, about 8 to about 14, about 9 to about 12, and about 10 to about 11 bases.

Sequencing probes of the present invention are designed to be complementary, and in general, perfectly complementary, to a sequence of the target sequence such that hybridization of a portion target sequence and probes of the present invention occurs. In particular, it is important that the interrogation position base and the detection position base be perfectly complementary and that the methods of the invention do not result in signals unless this is true.

In many embodiments, sequencing probes are perfectly complementary to the target sequence to which they hybridize; that is, the experiments are run under conditions that favor the formation of perfect basepairing, as is known in the art. As will be appreciated by those in the art, a sequencing probe that is perfectly complementary to a first domain of the target sequence could be only substantially complementary to a second domain of the same target sequence; that is, the present invention relies in many cases on the use of sets of probes, for example, sets of hexamers, that will be perfectly complementary to some target sequences and not to others.

In some embodiments, depending on the application, the complementarity between the sequencing probe and the target need not be perfect; there may be any number of base pair mismatches, which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the sequencing probes are sufficiently complementary to the target sequences to hybridize under normal reaction conditions. However, for most applications, the conditions are set to favor probe hybridization only if perfectly complementarity exists. Alternatively, sufficient complementarity is required to allow the ligase reaction to occur; that is, there may be mismatches in some part of the sequence but the interrogation position base should allow ligation only if perfect complementarity at that position occurs.

In some cases, in addition to or instead of using degenerate bases in probes of the invention, universal bases which hybridize to more than one base can be used. For example, inosine can be used. Any combination of these systems and probe components can be utilized.

Sequencing probes of use in methods of the present invention are usually detectably labeled. By "label" or "labeled" herein is meant that a compound has at least one element, isotope or chemical compound attached to enable the detection of the compound. In general, labels of use in the invention include without limitation isotopic labels, which may be radioactive or heavy isotopes, magnetic labels, electrical labels, thermal labels, colored and luminescent dyes, enzymes and magnetic particles as well. Dyes of use in the invention may be chromophores, phosphors or fluorescent dyes, which due to their strong signals provide a good signal-to-noise ratio for decoding. Sequencing probes may also be labeled with quantum dots, fluorescent nanobeads or other constructs that comprise more than one molecule of the same fluorophore. Labels comprising multiple molecules of the same fluorophore will generally provide a stronger signal and will be less sensitive to quenching than labels comprising a single molecule of a fluorophore. It will be understood that any discussion herein of a label comprising a fluorophore will apply to labels comprising single and multiple fluorophore molecules.

Many embodiments of the invention include the use of fluorescent labels. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, CASCADE BLUE®, Texas Red, and others described in the 6th Edition of the Molecular Probes Handbook by Richard P. Haugland, hereby expressly incorporated by reference in its entirety for all purposes and in particular for its teachings regarding labels of use in accordance with the present invention. Commercially available fluorescent dyes for use with any nucleotide for incorporation into nucleic acids include, but are not limited to: Cy3, Cy5, (Amersham Biosciences, Piscataway, N.J., USA), fluorescein, tetramethylrhodamine-, TEXAS RED®, CASCADE BLUE®, BODIPY® FL-14, BODIPY®R, BODIPY® TR-14, RHODAMINE GREEN™, OREGON GREEN® 488, BODIPY® 630/650, BODIPY® 650/665-, ALEXA FLUOR® 488, ALEXA FLUOR® 532, ALEXA FLUOR® 568, ALEXA FLUOR® 594, ALEXA FLUOR® 546 (Molecular Probes, Inc. Eugene, Oreg., USA), QUASAR® 570, QUASAR® 670, Cal Red 610 (BioSearch Technologies, Novato, Ca). Other fluorophores available for post-synthetic attachment include, inter alia, ALEXA FLUOR® 350, ALEXA FLUOR® 532, ALEXA FLUOR® 546, ALEXA FLUOR® 568, ALEXA FLUOR® 594, ALEXA FLUOR® 647, BODIPY® 493/503, BODIPY® FL, BODIPY® R6G, BODIPY® 530/550, BODIPY® TMR, BODIPY® 558/568, BODIPY® 558/568, BODIPY® 564/570, BODIPY® 576/589, BODIPY® 581/591, BODIPY® 630/650, BODIPY® 650/665, CASCADE BLUE®, CASCADE YELLOW™, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). In some embodiments, the labels used include fluoroscein, Cy3, Texas Red, Cy5, QUASAR® 570, QUASAR® 670 and Cal Red 610 are used in methods of the present invention.

Labels can be attached to nucleic acids to form the labeled sequencing probes of the present invention using methods known in the art, and to a variety of locations of the nucleosides. For example, attachment can be at either or both termini of the nucleic acid, or at an internal position, or both. For example, attachment of the label may be done on a ribose of the ribose-phosphate backbone at the 2' or 3' position (the latter for use with terminal labeling), in one embodiment through an amide or amine linkage. Attachment may also be made via a phosphate of the ribose-phosphate backbone, or to the base of a nucleotide. Labels can be attached to one or both ends of a probe or to any one of the nucleotides along the length of a probe.

Sequencing probes are structured differently depending on the interrogation position desired. For example, in the case of sequencing probes labeled with fluorophores, a single position within each sequencing probe will be correlated with the identity of the fluorophore with which it is labeled. Generally, the fluorophore molecule will be attached to the end of the sequencing probe that is opposite to the end targeted for ligation to the anchor probe.

Figure 5:
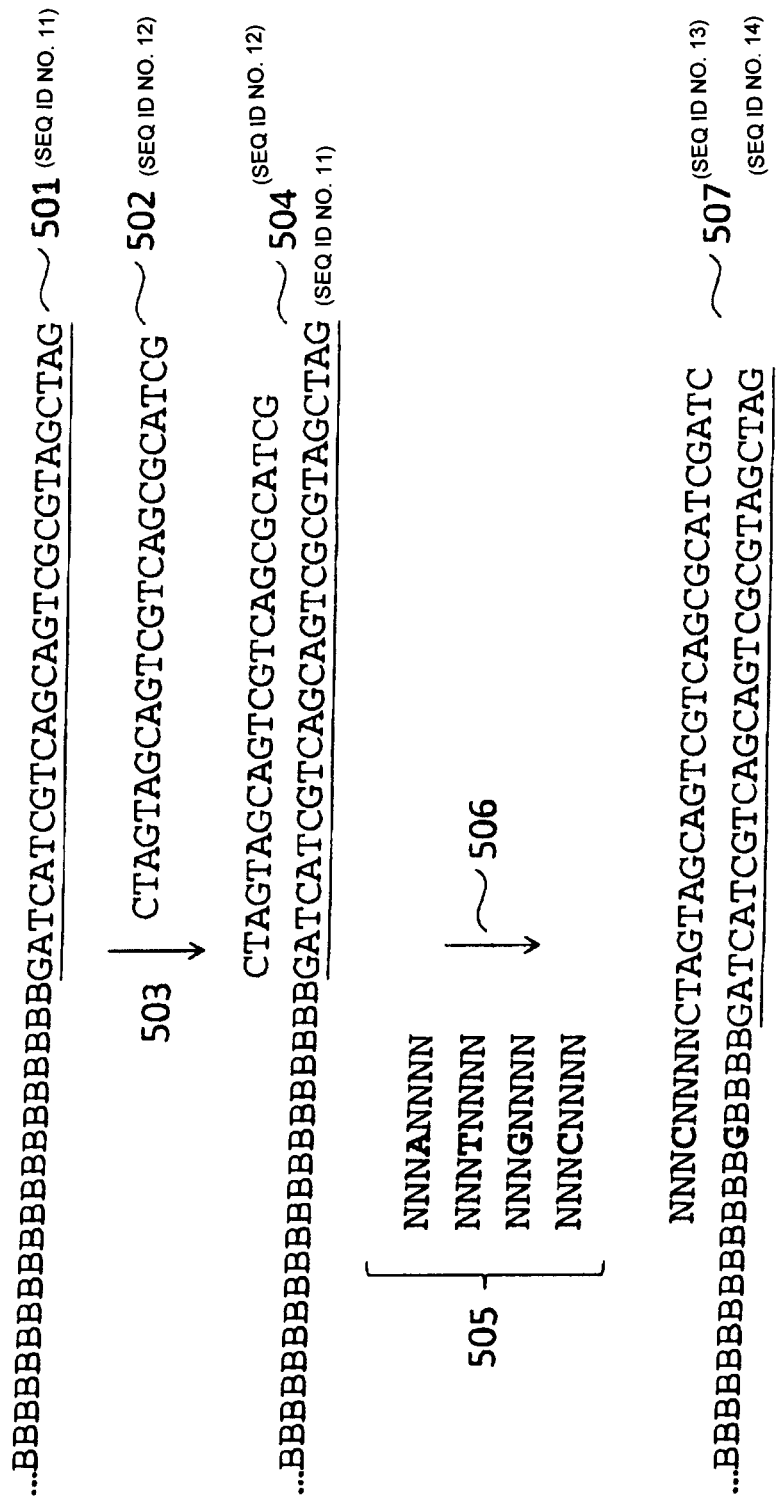
FIG. 5 is a schematic illustration of an embodiment of sequencing methods of the invention. Sequence legend: 501 (SEQ ID NO:11); 502 (SEQ ID NO:12); 504 (SEQ ID NO:11, SEQ ID NO:12); 507 (SEQ ID NO:13, SEQ ID NO:14).

By "anchor probe" as used herein is meant an oligonucleotide designed to be complementary to at least a portion of an adaptor, referred to herein as "an anchor site". Adaptors can contain multiple anchor sites for hybridization with multiple anchor probes, as described herein. As discussed further herein, anchor probes of use in the present invention can be designed to hybridize to an adaptor such that at least one end of the anchor probe is flush with one terminus of the adaptor (either "upstream" or "downstream", or both). In further embodiments, anchor probes can be designed to hybridize to at least a portion of an adaptor (a first adaptor site) and also at least one nucleotide of the target nucleic acid adjacent to the adaptor ("overhangs"). As illustrated in FIG. 5, anchor probe 502 comprises a sequence complementary to a portion of the adaptor. Anchor probe 502 also comprises four degenerate bases at one terminus. This degeneracy allows for a portion of the anchor probe population to fully or partially match the sequence of the target nucleic acid adjacent to the adaptor and allows the anchor probe to hybridize to the adaptor and reach into the target nucleic acid adjacent to the adaptor regardless of the identity of the nucleotides of the target nucleic acid adjacent to the adaptor. This shift of the terminal base of the anchor probe into the target nucleic acid shifts the position of the base to be called closer to the ligation point, thus allowing the fidelity of the ligase to be maintained. In general, ligases ligate probes with higher efficiency if the probes are perfectly complementary to the regions of the target nucleic acid to which they are hybridized, but the fidelity of ligases decreases with distance away from the ligation point. Thus, in order to minimize and/or prevent errors due to incorrect pairing between a sequencing probe and the target nucleic acid, it can be useful to maintain the distance between the nucleotide to be detected and the ligation point of the sequencing and anchor probes. By designing the anchor probe to reach into the target nucleic acid, the fidelity of the ligase is maintained while still allowing a greater number of nucleotides adjacent to each adaptor to be identified. Although the embodiment illustrated in FIG. 5 is one in which the sequencing probe hybridizes to a region of the target nucleic acid on one side of the adaptor, it will be appreciated that embodiments in which the sequencing probe hybridizes on the other side of the adaptor are also encompassed by the invention. In FIG. 5, "N" represents a degenerate base and "B" represents nucleotides of undetermined sequence. As will be appreciated, in some embodiments, rather than degenerate bases, universal bases may be used. It will be appreciated that FIG. 5 illustrates only one exemplary embodiment of sequencing by ligation methods of use in the present invention. Further embodiments are described in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, each of which is hereby incorporated in its entirety for all purposes and in particular for all teachings related to different embodiments of sequencing by ligation using combinations of anchor and sequencing probes.

Anchor probes of the invention may comprise any sequence that allows the anchor probe to hybridize to a DNB, generally to an adaptor of a DNB. Such anchor probes may comprise a sequence such that when the anchor probe is hybridized to an adaptor, the entire length of the anchor probe is contained within the adaptor. In some embodiments, anchor probes may comprise a sequence that is complementary to at least a portion of an adaptor and also comprise degenerate bases that are able to hybridize to target nucleic acid regions adjacent to the adaptor. In some exemplary embodiments, anchor probes are hexamers that comprise 3 bases that are complementary to an adaptor and 3 degenerate bases. In some exemplary embodiments, anchor probes are 8-mers that comprise 3 bases that are complementary to an adaptor and 5 degenerate bases. In further exemplary embodiments, particularly when multiple anchor probes are used, a first anchor probe comprises a number of bases complementary to an adaptor at one end and degenerate bases at another end, whereas a second anchor probe comprises all degenerate bases and is designed to ligate to the end of the first anchor probe that comprises degenerate bases. It will be appreciated that these are exemplary embodiments, and that a wide range of combinations of known and degenerate bases can be used to produce anchor probes of use in accordance with the present invention.

The present invention provides sequencing by ligation methods for identifying sequences of DNBs. In certain aspects, the sequencing by ligation methods of the invention include providing different combinations of anchor probes and sequencing probes, which, when hybridized to adjacent regions on a DNB, can be ligated to form probe ligation products. The probe ligation products are then detected, which provides the identity of one or more nucleotides in the target nucleic acid. By "ligation" as used herein is meant any method of joining two or more nucleotides to each other. Ligation can include chemical as well as enzymatic ligation. In general, the sequencing by ligation methods discussed herein utilize enzymatic ligation by ligases. Such ligases invention can be the same or different than ligases discussed above for creation of the nucleic acid templates. Such ligases include without limitation DNA ligase I, DNA ligase II, DNA ligase III, DNA ligase IV, E. coli DNA ligase, T4 DNA ligase, T4 RNA ligase 1, T4 RNA ligase 2, T7 ligase, T3 DNA ligase, and thermostable ligases (including without limitation Taq ligase) and the like. As discussed above, sequencing by ligation methods often rely on the fidelity of ligases to only join probes that are perfectly complementary to the nucleic acid to which they are hybridized. This fidelity will decrease with increasing distance between a base at a particular position in a probe and the ligation point between the two probes. As such, conventional sequencing by ligation methods can be limited in the number of bases that can be identified. The present invention increases the number of bases that can be identified by using multiple probe pools, as is described further herein.

A variety of hybridization conditions may be used in the sequencing by ligation methods of sequencing as well as other methods of sequencing described herein. These conditions include high, moderate and low stringency conditions; see for example Maniatis et al., Molecular Cloning: A Laboratory Manual, 2d Edition, 1989, and Short Protocols in Molecular Biology, ed. Ausubel, et al, which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays," (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

In any of the embodiments described herein, sequencing probes of the invention can be modified such that they hybridize to the target sequence and ligate to an adjacent anchor probe in a desired orientation. For example, in order to ensure that a set of sequencing probes will only ligate to an anchor probe such that their interrogation position is two bases 5' of the anchor probe, one end of the sequencing probes can be blocked such that ligation can only occur at the desired end. Such methods of modifying nucleic acids, including nucleic acid sequencing probes, to control for orientation and direction of ligation are known in the art and are also described in U.S. application Ser. Nos. 12/329,365 and 12/335,188, now U.S. Pat. No. 8,551,702; which are both herein incorporated by reference in their entirety for all purposes and in particular for all teachings related to controlling ligation of nucleic acid molecules to each other in a desired orientation.

IIIB. Increasing Efficiency in Base Calling in Sequencing Reactions

In one aspect, the present invention provides methods and compositions for improving the efficiency in base calling in sequencing reactions. By "base calling" herein is meant the ability to read a nucleotide at a particular detection position and is understood by those in the art. In some embodiments, the present invention provides methods and compositions for distinguishing among four different nucleotides using fewer than four labels. In further embodiments, the present invention provides methods and compositions for detecting two or more bases per sequencing reaction cycle. Such embodiments serve to improve the efficiency of base calling, because the reduction in the number of labels required in a particular sequencing reaction and the increase in the number of bases that can be read in a particular sequencing reaction cycle serves to reduce costs and time associated with sequencing target nucleic acids. Such a savings in time and costs can be of particular benefit when sequencing large numbers of nucleic acids, as is involved in applications such as whole genome sequencing.

As discussed above, conventional methods of sequencing will generally use four different labels to distinguish between the four possible bases at a specific location in a target sequence. The present invention utilizes fewer than four unique labels to distinguish between the four possible bases, thus increasing the speed and decreasing the cost of sequencing reactions. Using fewer than four labels to distinguish between four nucleotides also provides the ability to detect multiple bases in a sequencing reaction cycle without needing to use more than four labels. This is of particular use at the current state of the art, as most labels, particularly fluorescent labels, are harder to distinguish when more than four wavelengths (e.g. four colors) are used.

Although the following description is provided in terms of sequencing by ligation methods, particularly cPAL, it will be appreciated that the methods and compositions described herein can be used with any sequencing method known in the art, including sequencing by extension (also known as sequencing by synthesis) and sequencing by hybridization. For example, it will be apparent to one of skill in the art that probe sets such as those described in further detail below can be used in sequencing by extension reactions, with the variation that rather than sequencing probes, the labels will generally be attached to dNTPs. Such variations on the methods and compositions described herein could be made using standard and routine techniques by one of skill in the art and are therefore encompassed by the present invention.

In one embodiment, sequencing applications of the invention use sets of sequencing probes which are labeled in such a way as to distinguish between four nucleotides at a single detection position using only two different labels. Generally, in this embodiment, only two labels are used, generally fluorophores.

One example of this embodiment is illustrated in FIG. 2. In FIG. 2, set 202 is an example of a probe set that is useful in methods where two labels are used to read four bases. As shown in 202, the A probe is labeled with a first label (identified as C1), the T probe (or U probe, if desirable) is labeled with a second label (C2), the C probe is labeled with both the first and the second label (C1+C2), and the G probe is not labeled. As will be appreciated by those in the art, any combination or variation can be used (e.g. the T probe labeled with C1, the C probe labeled with C2, the A probe labeled with C1+C2, etc.). In sequencing applications utilizing a probe set such as that pictured in 202, the presence of the G probe is assumed when no label can be detected. The labels on probes such as those pictured in FIG. 2 can be any kind of detectable label known in the art as described more fully below, and in specific cases, fluorescent labels are used.

As described more fully below, additional detection positions, e.g. multiple detection positions, can be detected in a variety of ways. In one embodiment, iterative cycles of these methods can be done to sequentially detect additional detection positions. That is, after ligation and detection of the labels present (which allows the identification of the base at the detection position), the ligated probes are released from the array and the process is repeated for a new detection position. In other embodiments, as more fully described below and in FIG. 2, 4 colors can be used to identify nucleotides at two detection positions simultaneously, for example at the "upstream" end of the adapter and at the "downstream" end of the adapter. In this embodiment, the first set of sequencing probes (e.g. the "upstream" set) uses two different labels (e.g. a first and a second label) and the second set of sequencing probes (e.g. the "downstream" set) uses two different labels (e.g. a third and a fourth label). As will be appreciated by those in the art, in this embodiment, frequently the "non-ligation" terminus will be blocked such that ligation cannot occur at one terminus. For example, in the probes (204) shown in FIG. 2, the 5' end of the first set is blocked such that ligation at the 5' end cannot occur, and the same for the 3' ends of the second set. This prevents a probe from the first set hybridizing to the wrong terminus of the adapter, which could lead to ambiguity. In other embodiments, also as described herein, the present invention allows the identification of two detection positions simultaneously, even if not "upstream" and "downstream" of a single adapter. That is, these techniques can be used to identify detection positions adjacent to two different adapters of the concatamer.

In general, the unique labels can be generated in a number of ways. As shown above, two labels can be used to label 4 probe sets: dye1, dye 2, dye1+2, and nodye. Alternatively, the intensity of the label can be used to create unique labels. For example, a probe set may comprise unique label1 as dye1 used at 1× intensity, label2 is dye1 used at 2× intensity, label3 is dye used at 10× intensity, and label4 can be nodye. This embodiment can be done in two general ways. In one embodiment, each probe can comprise one or more labels; e.g. probe1 has one fluorophore per probe, probe2 has two fluorophores per probe, and probe3 has 10 fluorophores per probe. However, due to both the expense of the dyes and the crosstalk (including quenching) that can occur with multiple labels per probe, another embodiment utilizes probe sets such that only a portion of the set is labeled. That is, probe1 can have 10% of the set labeled with one fluorophore, and the rest are unlabeled (e.g. label1 is 0.1× dye), probe2 can have 50% of the set labeled with one fluorophore, and the rest are unlabeled (e.g. label2 is 0.5× dye), and probe3 can have 100% of the probes labeled. This results in a relative intensity difference serving as the unique label. As will be appreciated by those in the art, these methods can also be combined, where different dyes at different intensities are used (e.g. probe1 is dye1 at 10% coverage, probe2 is dye1 at 100% coverage, probe3 is dye2 at 10% coverage, and probe4 is dye 2 at 100% coverage, etc.). Any and all combinations are contemplated herein.

In addition, as more fully outlined below, dissociative labels can be used to increase the confidence of a base call; in this embodiment, a read is done (e.g. in the case of fluorophores, an image of the array is collected) and then the conditions are changed to disassociate one of the labels, and a second image is taken.

Thus, sequencing applications using the nucleic acid nanoballs of the invention can detect more than two bases in a target nucleic acid by utilizing probes that can only hybridize to one side of an adaptor or the other. For example, in FIG. 2, set 204 is premised along the same lines as set 202, except that with set 204, four different labels are used to distinguish between 8 different nucleotides—i.e., to identify which base is present at two different locations in a target sequence. As discussed above, nucleic acid nanoballs of the invention comprise repeating units of target sequence and adaptors. In specific examples of sequencing applications of the invention, four of the probes in set 204 are 3' probes, i.e., they can hybridize to locations of the target sequence 3' to an adaptor, whereas the other four probes are 5' probes and hybridize only to locations 5' to an adaptor. Similar to the labeling scheme of set 202 discussed above, the 5' probes of set 204 has an A probe labeled with a first label (C1), a T probe labeled with a second label (C2), a C probe labeled with the first and second labels (C1+C2) and a G probe that has no label. In addition, the 3' probes of set 204 has an A probe labeled with a third label (C3), a T probe labeled with a fourth label (C4), a C probe labeled with both the third and fourth label (C3+C4), and again the G probe is unlabeled. By structuring the probes in this way, a set such as probe set 204 can be used to identify the nucleotide at two different positions of a target sequence.

In certain cases, the nucleotides at four different positions of a target sequence in a nucleic acid nanoball are identified by using four probe sets in a single sequencing cycle to read two bases from each side of an adaptor. One example of such a sequencing application is illustrated in FIG. 6, which shows an exemplary portion of a nucleic acid nanoball 602 with adaptors on each of the 5' and 3' ends (shaded "b"s) and target nucleic acid to be sequenced in between the adaptors (i.e., in between the shaded regions). In addition, sequencing probes are shown that would allow for reading of the four bases from 5' and 3' of the two adaptors shown in two cycles (again, with optional blocking to prevent ligation at the incorrect end). In the method of sequencing illustrated in FIG. 6, probe sets of the type shown in FIG. 2 at 204 are used; however, four probe sets are used in a single reaction to read two bases from each side. In FIG. 6, "G", "T", "A" and "C" are specific nucleotide bases and "N"s are universal or degenerate bases. In a first cycle of sequencing, four probes sets 620 are used. A sequencing probe that would identify the G in the target nucleic acid immediately 3' to the end of the 5' adaptor is shown at 604 (CNNNNNN-C1/C2). Such a sequencing probe would be part of a first set 622: CNNNNNN-C1/C2; ANNNNNN-C1; TNNNNNN-C2 and GNNNNNN (see FIG. 6B for the probe sets that would be used in each of the two rounds of sequencing). The sequencing probe that would identify the T in the target nucleic acid two bases from the 3' end of the 5' adaptor is shown at 606 (NANNNNN‡C1), and would be part of a second set 624: NANNNNN‡C1; NTNNNNN‡C2; NGNNNNN; and NCNNNNN‡C1C2, where the symbol "‡" denotes a cleavage site). A broad variety of cleavable moieties are available in the art of solid phase and microarray oligonucleotide synthesis, including photocleavable moieties (see, e.g., Pon, R. (1993), Methods Mol. Biol. 20:465-496; Verma et al. (1998), Annu. Rev. Biochem. 67:99-134; and U.S. Pat. Nos. 5,739,386 and 5,700,642). Again, using a G probe in this instance is optional, since the G probe does not have a label.

A sequencing probe that would identify the C in the target nucleic acid immediately 5' to the end of the 3' adaptor is shown at 612 (NNNNNNG). Such a sequencing probe would be part of a third set 626: NNNNNNG; C3/C4-NNNNNC; C31-NNNNNA; and C4-NNNNNT. The sequencing probe that would identify the A in the target nucleic acid two bases from the 5' end of the 3' adaptor is shown at 614 (C4‡NNNNTN), and would be part of a fourth set 628: C4‡NNNNTN; C3‡NNNNAN; NNNNNGN; and C3C4‡NNNNCN, again, where the symbol "‡" denotes a cleavage site. The first, second, third and fourth sequencing probe sets are used together to sequence four bases at a time in the following manner: Anchor probes are allowed to hybridize to the adaptors in the library constructs after which (or simultaneously) all four sets of sequencing probes are added and allowed to hybridize to the target nucleic acid. The adjacently-hybridized anchor probes and sequencing probes may then be ligated to one another if the sequencing probe is complementary to the target nucleic acid in the library construct. An extensive wash is performed to eliminate unligated sequencing probes. Two sequencing probes will ligate to the anchor probes that hybridized to the 5' adaptor (one sequencing probe from the first sequencing probe set (604) and one sequencing probe from the second sequencing probe set (606)), and two sequencing probes will ligate to anchor probes that hybridized to the 3' adaptor (one sequencing probe from the third sequencing probe set (612) and one sequencing probe from the fourth sequencing probe set (614)). It should be noted that more than one sequencing probe will not ligate to a single anchor probe, but about half of the 5' anchor probes will ligate to sequencing probes from the first set, and about half of the 5' anchor probes will ligate to sequencing probes from the second set. Similarly, about half of the 3' anchor probes will ligate to sequencing probes from the third set, and about half of the 5' anchor probes will ligate to sequencing probes from the fourth set.

The fluorescent signal for the first read out in this hypothetical would be C1+C2+C1 from the 5' side and no color (from the G sequencing probe)+C4 from the 3' side. The sequencing reaction mix is then subjected to cleaving at the "‡" site, eliminating the fluorescent signal from the sequencing probes interrogating the bases in the target nucleic acid two nucleotides from the ligation junction (i.e., sequencing probes from the second and fourth sequencing probe sets). A wash is then performed, and the fluorescent signal is read again. The fluorescent signal for the second read out in this hypothetical would be C1+C2 from the 5' side and no color from the 3' side. That is, the strong C1 signal contributed by the NANNNNN‡CL sequencing probe (606) and the C4 signal contributed by the C2‡NNNNNTN sequencing probe (614) will have disappeared. The disappearance of a strong C1 signal indicates that a T is two bases from the 3' end of the 5' adaptor (the A sequencing probe from the second set ligated to the anchor probe). The disappearance of the C4 signal indicates that an A is two bases from the 5' end of the 3' adaptor (the T sequencing probe from the fourth set ligated to the anchor probe). The remaining C1+C2 signal indicates that a G is in the first position in the target nucleic acid immediately 3' to the end of the 5' adaptor (the C sequencing probe from the first set ligated to the anchor probe) and that there is no color at all from the third sequencing probe set indicates that a C is the first base in the target nucleic acid immediately 5' to the end of the 3' adaptor (the G sequencing probe from the third set ligated to the anchor probe).

In a second cycle of sequencing in this hypothetical, the third and fourth nucleotides in the target nucleic acid 3' to the end of the 5' adaptor and the third and fourth nucleotides in the target nucleic acid 5' to the end of the 3' adaptor are read simultaneously using a second group of four probe sets 630. A sequencing probe that would identify the A in the target nucleic acid three bases 3' from the end of the 5' adaptor is shown at 608 (NNTNNNN-C2). Such a sequencing probe would be part of a fifth set 632: NNTNNNN-C2; NNANNNN-C1; NNCNNNN-C1C2 and NNGNNNN. The sequencing probe that would identify the C in the target nucleic acid four bases 3' from the end of the 5' adaptor is shown at 610 (NNNGNNN), and would be part of a sixth set 634: NNNGNNN; NNNANNN‡CL; NNNTNNN‡C2 and NNNCNNN‡C1C2, where the symbol "‡" denotes a cleavage site. The sequencing probe that would identify the T in the target nucleic acid three bases 5' from the end of the 3' adaptor is shown at 616 (C3-NNNNANN). Such a sequencing probe would be part of a seventh set 636: C3-NNN-NANN; C4-NNNNTNN; C3C4-NNNNCNN; and NNNNGNN. The sequencing probe that would identify the G in the target nucleic acid four bases 5' from the end of the 3' adaptor is shown at 618 (C3C4‡NNNCNNN), and would be part of an eighth set 638: C3C4‡NNNCNNN; C3‡NNNANNN; NNNGNNN; and C4‡NNNTNNN, again, where the symbol "‡" denotes a cleavage site.

As before, the fifth, sixth, seventh and eighth sequencing probe sets can be used together to sequence four bases at a time in the following manner: Anchor probes are allowed to hybridize to the adaptors in the library constructs after which (or simultaneously) all four sets of sequencing probes are added and allowed to hybridize to the target nucleic acid. The adjacently-hybridized anchor probes and sequencing probes may be ligated to one another, providing additional hybridization stability to the sequencing probes complementary to the target nucleic acid. An extensive wash is performed to eliminate unligated sequencing probes. Two sequencing probes will ligate to the anchor probes that hybridized to the 5' adaptor (one sequencing probe from the first sequencing probe set (604) and one sequencing probe from the second sequencing probe set (606)), and two sequencing probes should ligate to the anchor probes that hybridized to the 3' adaptor (one sequencing probe from the third sequencing probe set (612) and one sequencing probe from the fourth sequencing probe set (614)).

The fluorescent signal for the first read out in this second round of sequencing hypothetical would be C2+no color from the 5' side and C3+C4 from the 3' side, with C3 in an approximately 2:1 ratio with C4. The sequencing reaction mix is then subjected to cleaving at the "‡" site, a wash is performed, and the fluorescent signal is then re-read. The fluorescent signal for the second read out in this hypothetical would be C2 from the 5' side and C3 only from the 3' side. That is, the no color signal contributed by the NNNGNNN sequencing probe (610) and the C3C4 signal contributed by the C3C4‡NNNCNNN sequencing probe (618) will have disappeared. The no change in C2 signal indicates that a C was in the fourth position in the target nucleic acid four nucleotides 3' from the end of the 5' adaptor (the G sequencing probe from the sixth set ligated to the anchor probe). The disappearance of the C4 signal and decreased relative intensity of the C3 signal indicates that an G was in the fourth position in the target nucleic acid 5' from the end of the 3' adaptor (the C sequencing probe from the eighth set ligated to the anchor probe). The no change in the remaining C2 signal indicates that an A was in the third position in the target nucleic acid 3' from the end of the 5' adaptor (the T sequencing probe from the fifth set ligated to the anchor probe) and remaining C3 signal indicates that a T was in the third position in the target nucleic acid 5' from the end of the 3' adaptor (the A sequencing probe from the seventh set ligated to the anchor probe). Though this particular aspect shows use of four sequencing probe sets, two from each of the 5' and 3' adaptor, other combinations may be employed; for example, all four probe sets could be used on the same adaptor, either 5' or 3', and the like, though reading from 5' from two different adaptors or reading 3' from two different adaptors would not work in this aspect. Further, fifth and sixth labels may be used with fifth and sixth sets of sequencing probes to acquire sequence from yet another adaptor or from a different direction on an adaptor being employed with the first and second or third and fourth sets of sequencing probes, and so on with seventh and eighth labels and sequencing sets.

FIG. 3 discloses probes that could be used in yet another embodiment of the sequencing methods herein. As in the methods shown and described in FIG. 6, four bases may be read per cycle using four colors and three images, resulting in four-fold fewer cycles and one-quarter less images than with methods used currently in the art. In brief, the method shown in FIG. 3 reads two bases for each of 5' and 3' anchors such as shown in FIG. 6, but rather than utilizing a cleavable moiety, the different optically-discernable tags have different $T_m$'s and this property is exploited by using discriminating washes between imaging events, i.e., by dissociating the tags from the sequencing probes. A set of sequencing probes is shown at 302. Each sequencing probe comprises a sequencing portion (301, 303, 305, and 307) with a interrogation nucleotide (here at the 1 position, respectively, A, T, C, G), a tail (304, 308, 312, and 316) a tail complement (306, 310, 314 and 318) with each tail complement comprising a label (309, 311, 313 and 315). Note that the tail and tail complement (304 and 306) for the "A" sequencing probe (301) is of a relative length 4x, the tail and tail complement (308 and 310) for the "T" sequencing probe (303) is of a relative length 3x, the tail and tail complement (312 and 314) for the "C" sequencing probe (305) is of a relative length 2x, and the tail and tail complement (316 and 318) for the "G" sequencing probe (307) is of a relative length 1× (alternatively, the G probe can be unlabelled). Shown here, both the tails and the tail complements are shown to be of relative length 4x, 3x, 2x, and 1x. However, in alternative aspects, the tails may the same or of similar lengths, and only the tail complements vary in length. Also, in some alternative aspects, the label for one of the sequencing probes in a set will not be dissociable from the sequencing probe.

Two 5' sequencing probe sets are used and two 3' sequencing probe sets are used. The first sequencing probe set will interrogate the first base immediately 3' to the end of the 5' adaptor (namely, $GN_6X_3$, $CN_6X_5$, $TN_6X_7$ and $AN_6X_9$); the second sequencing probe set will interrogate the second base 3' from the end of the 5' adaptor (namely, $NGN_5X_3$, $NCN_5X_5$, $NTN_5X_7$ and $NAN_5X_9$); the third sequencing probe set will interrogate the first base immediately 5' to the end of the 3' adaptor (namely $X_3N_6G$, $X_5N_6C$, $X_7N_6T$ and $X_9N_6A$); and the fourth sequencing probe set will interrogate the second base 5' from the end of the 3' adaptor (namely $X_3N_5GN$, $X_5N_5CN$, $X_7N_5TN$ and $X_9N_5AN$). Here, "G", "C", "T" and "A" are specific bases, "N"s are degenerative bases in the sequencing probes, "X"s are bases in the tail portions of the sequencing probes, "Y"s are complementary sequences in the tail complements to the "X" sequences in the tails, and C1, C2, C3 and C4 are different colors (e.g., fluorophores).

In methods using sequencing probe sets as shown here in FIG. 3, the first, second, third and fourth sequencing probe sets are used together to sequence four bases at a time: Anchor probes are allowed to hybridize to the adaptors in library constructs after which (or simultaneously) all four sets of sequencing probes are added, allowed to hybridize to the target nucleic acid, and then are ligated to the adjacently-hybridized anchor probes. An extensive wash is performed to eliminate unligated sequencing probes. As in the methods described for FIG. 6, two sequencing probes should ligate to anchor probes that hybridized to the 5' adaptor (one from the first sequencing probe set and one from the second sequencing probe set), and two sequencing probes should ligate to anchor probes that hybridized to the 3' adaptor (one from the third sequencing probe set and one from the fourth sequencing probe set). Again, no more than one sequencing probe will ligate to an anchor probe, but about half of the 5' anchor probes will ligate to sequencing probes from the first set, and about half of the 5' anchor probes will ligate to sequencing probes from the second set. Similarly, about half of the 3' anchor probes will ligate to sequencing probes from the third set, and about half of the 5' anchor probes will ligate to sequencing probes from the fourth set.

In an embodiment where the G sequencing probe from the first set hybridized to the target nucleic acid and ligated to the 5' anchor, the T sequencing probe from the second set hybridized to the target nucleic acid and ligated to the 5' anchor, the A sequencing probe from the third set hybridized to the target nucleic acid and ligated to the 3' anchor and the C sequencing probe from the fourth set hybridized to the target nucleic acid and ligated to the 3' anchor, the fluorescent signal would be C1+C2 from the 5' side and C3+C4 from the 3' side. The sequencing reaction mix is then subjected to a discriminating wash at a temperature where the short "G" tail complements will be washed away, and the fluorescent signal is then re-read. The fluorescent signal for the second read out in this hypothetical would be C2+C3+C4, indicating that the C1-associated sequencing probe (the label associated with the first set of sequencing probes) was a G. Next, a second discriminating wash is performed at a temperature that would remove the C sequencing probes. Again an image is taken, and the third read out would be C2+C3, indicating that the C4-associated sequencing probe (from the fourth set of sequencing probes) was a C. A third discriminating wash is then performed at a temperature that would remove the T sequencing probes. Another image is taken and the last read out is C3, indicating that the C2-associated sequencing probe was a T (the label associated with the second set of sequencing probes), and the C3-associated sequencing probe is an A. Again, though this particular embodiment shows use of four sequencing probe sets, two from each of the 5' and 3' adaptor, other combinations may be employed; for example, all four probe sets could be used on the same adaptor, either 5' or 3', and the like. Further, fifth and sixth labels may be used with fifth and sixth sets of sequencing probes to acquire sequence from yet another adaptor or from a different direction on an adaptor being employed with the first and second or third and fourth sets of sequencing probes, and so on with seventh and eighth labels and sequencing sets.

FIG. 4 shows sequencing probe sets that may be useful in still further embodiments of the invention. As in the methods shown and described in FIGS. 6 and 3, four bases may be read per cycle using four colors. In certain embodiments, a single image may be taken to distinguish all four bases, resulting in a four-fold reduction in the number of images that must be acquired overall. In brief, the method shown in FIG. 8 reads two bases for each of 5' and 3' anchors such as shown in FIGS. 6 and 3, but rather than utilizing a cleavable moiety or tail complements with different $T_m$'s, each optically-discernable tag, e.g., fluorophore, has 4 different levels of brightness associated with one of the nucleotides A, T, C or G. In this embodiment, two 5' sequencing probe sets are used. The first set will interrogate the first base immediately 3' to the end of the 5' adaptor (namely, $GN_6$, $CN_6C1$, $TN_6C1^+$ and $AN_6C1^{+2}$); the second set will interrogate the second base 3' from the end of the 5' adaptor (namely, $NGN_5$, $NCN_5C2$, $NTN_5C2^+$ and $NAN_5C2^{+2}$), the third set will interrogate the first base immediately 5' from the end of the 3' adaptor (namely $N_6G$, $C3N_6C$, $C3^+N_6T$ and $C3^{+2}N_6A$); and the fourth set will interrogate the second base 5' from the end of the 3' adaptor (namely $N_5GN$, $C4N_5CN$, $C4^+N_5TN$ and $C4^{+2}N_5AN$). As before, "G", "C", "T" and "A" are specific bases, "N"s are degenerative bases in the sequencing probes, C1, C2, C3 and C4 are different colors (e.g., fluorophores), and, e.g., C1, $C1^+$ and $C1^{+2}$ differ in brightness or intensity of the fluorophore.

In methods using sequencing probe sets as shown here in FIG. 4, the first, second, third and fourth sequencing probe sets are used together to sequence four bases at a time: Anchor probes are allowed to hybridize to the adaptors in library constructs after which all four sets of sequencing probes are added, allowed to hybridize to the target nucleic acid, and then are ligated to the adjacently-hybridized anchor probes. An extensive wash is performed to eliminate unligated sequencing probes. As in the methods described for FIGS. 6 and 3, two sequencing probes should ligate to anchors that hybridized to the 5' adaptor (one from the first sequencing probe set and one from the second sequencing probe set), and two sequencing probes should ligate to anchor probes that hybridized to the 3' adaptor (one from the third sequencing probe set and one from the fourth sequencing probe set). Again, no more than one sequencing probe will ligate to each anchor, but about half of the 5' anchor probes will ligate to sequencing probes from the first set, and about half of the 5' anchor probes will ligate to sequencing probes from the second set. Similarly, about half of the 3' anchor probes will ligate to sequencing probes from the third set, and about half of the 3' anchors will ligate to sequencing probes from the fourth set.

In an embodiment in which the G sequencing probe from the first set hybridized to the target nucleic acid and ligated to the 5' anchor, the T sequencing probe from the second set hybridized to the target nucleic acid and ligated to the 5' anchor, the A sequencing probe from the third set hybridized to the target nucleic acid and ligated to the 3' anchor and the C sequencing probe from the fourth set hybridized to the target nucleic acid and ligated to the 3' anchor, the fluorescent signal would be $C2^+$ from the 5' side and $C3^{+2}+C4$ from the 3' side, corresponding to a target sequence of CA immediately adjacent to the 5' adaptor (with the G sequencing probe from the first set providing no color and the T sequencing probe from the second set providing C2+) and TG immediately adjacent to the 3' adaptor (with the A sequencing probe from the third set providing $C3^{+2}$ and the C sequencing probe from the fourth set providing C4).

Figure 8:
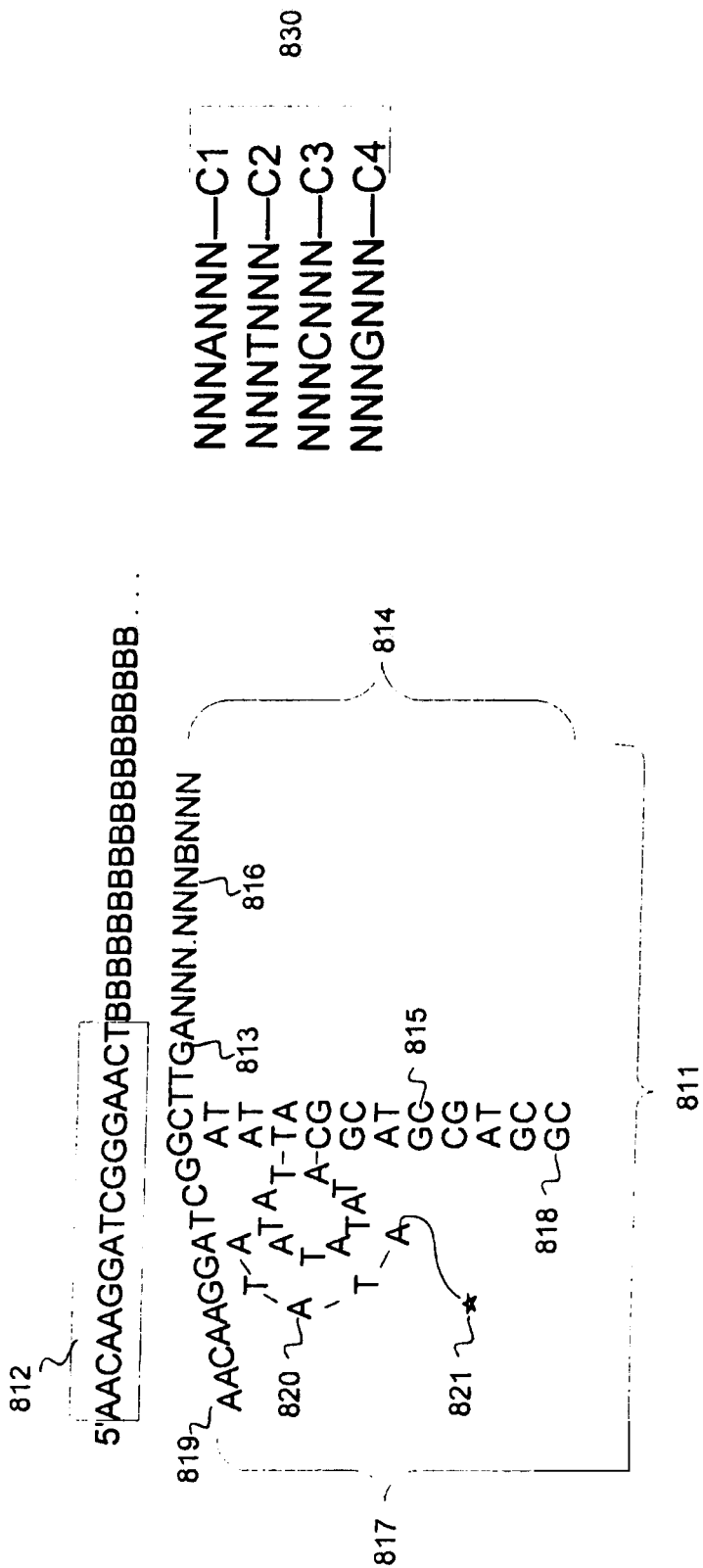
FIG. 8 is a schematic illustration of an embodiment of sequencing methods of the invention. Sequence legend: 812 (SEQ ID NO:24); 816 (SEQ ID NO:25); 819 (SEQ ID NO:26).

The intensity difference between the fluorophores may be achieved by differing concentrations of the A, T, C, G sequencing probes within each set, or by varying lengths of the sequencing probes within each set (e.g., by using more degenerate or universal bases), or by using discriminatory modifications (e.g., using PNAs or LNAs in varying amounts) for the sequencing probes in each set. In preferred aspects, the intensity difference is achieved by attaching a different number of fluorophores (or other tags), such as, e.g., 0, 1, 2 and 4 fluorophores per sequencing probe (e.g., zero labels on the G sequencing probe, one label on the T sequencing probe, two labels on the A sequencing probe, and four labels on the C sequencing probe), or 0, 1, 3 and 6-9 fluorophores per sequencing probe (e.g., zero labels on the G sequencing probe, one label on the T sequencing probe, three labels on the A sequencing probe, and six to nine labels on the C sequencing probe). As yet another alternative, the same could be achieved with dyes with the same emission wavelength but with different brightnesses. Although in the embodiment pictured in FIG. 4, the C probe is associated with the fluorophore with a 1× brightness, in some aspects the C probe is associated with the brightest fluorophores (e.g., fluorophore with the 4× brightness) as it has been observed that C has minimal cross talk with other bases. G is shown in FIG. 8 to be the nucleotide that is not associated with a fluorophore, which is preferred in many aspects as it has been observed that G is prone to cross talk. T, in some aspects would be the 1× probe (e.g., C1) and A would be the 2× probe (e.g., C1+). Overall, that is, a scheme of C>A>T>G would be used in some aspects. In still further embodiments, different levels of intensities can be achieved by varying the number of probes within a set that comprise a particular label. For example, if A probes should show greater intensity than T probes, one way to achieve this distinction is by labeling a larger relative number of the A probes in the set with a label than T probes, such that in a sequencing reaction overall, a larger percentage of the A probes will be labeled than the T probes, and thus the signal associated with a base call of "A" will have a higher intensity than the signal associated with a base call of "T".

Other aspects of the technology may be employed using labels of different intensities. In one implementation, four bases in one position may be read with two colors using two different intensities of the two colors. For example, a probe set where the A probe is labeled with C1, the T probe is labeled with C1+, the C probe is labeled with C2 and the G probe is labeled with C2+ may be employed in reactions where one base is read per reaction. Sequencing by synthesis methods may employ this scheme where one position is read per cycle. In implementations where two bases are read per reaction, one 5' from an adaptor and one 3' from the same or a different adaptor, an exemplary probe set may include a 5' A probe labeled with C1, a 5' T probe labeled with C1+, a 5° C. probe labeled with C2 and a 5' G probe labeled with C2+; and a 3' A probe labeled with C3, a 3' T probe labeled with C3+, a 3° C. probe labeled with C4 and a 3' G probe labeled with C4+.

Figure 11:
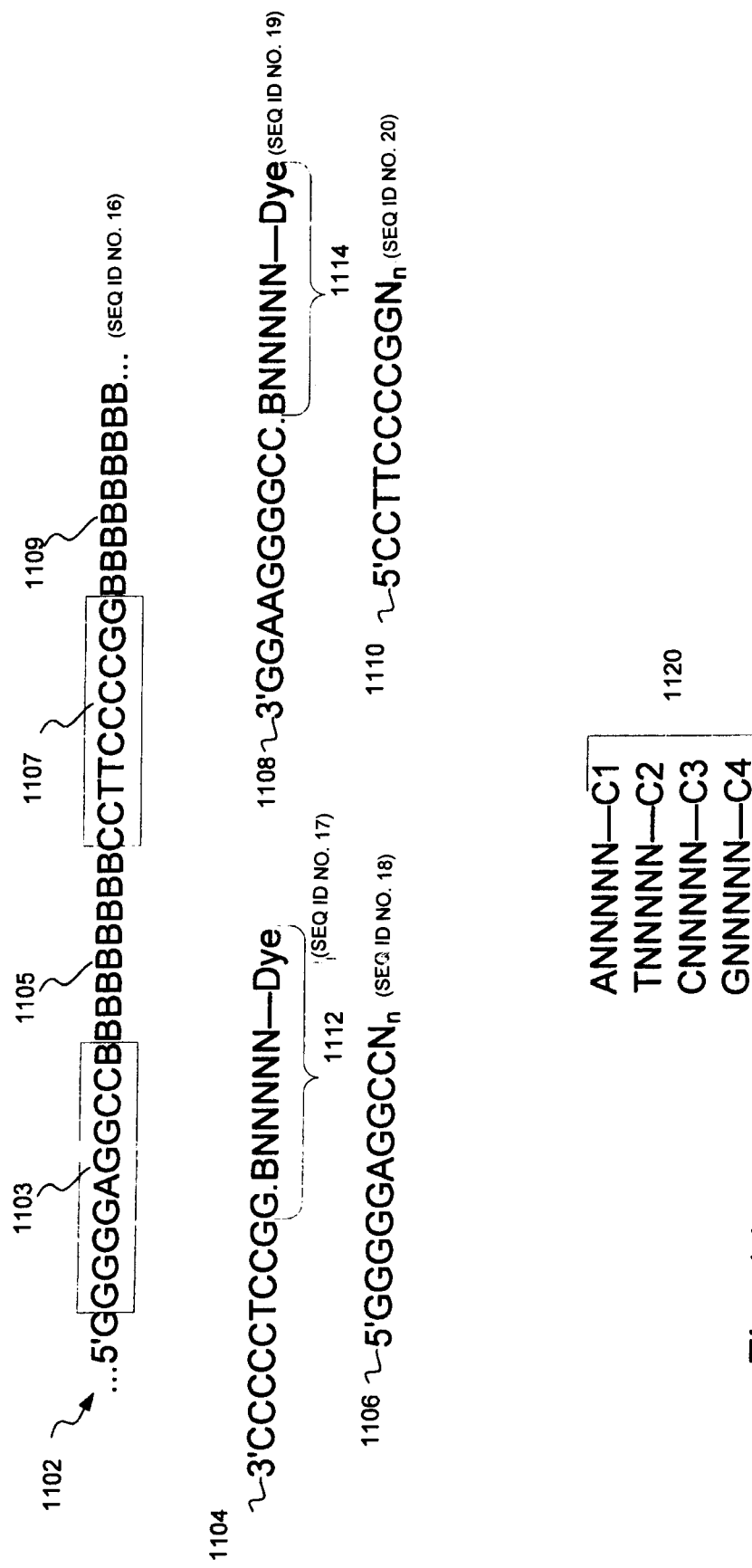
FIG. 11 is a schematic illustration of an embodiment of sequencing methods of the invention. Sequence legend: 1102 (SEQ ID NO:16); 1104 (SEQ ID NO:17); 1108 (SEQ ID NO:19); 1106 (SEQ ID NO:18); 1110 (SEQ ID NO:20).

In some embodiments, sequencing methods of the invention utilize invader oligonucleotides. FIG. 11 is a schematic illustration of a method for cPAL sequencing using invader oligonucleotides, where the invader oligonucleotides provide selective removal of each anchor probe/sequencing probe complex in a multiplexed reaction. A portion of a library construct is shown at 1102, comprising two adaptors (shaded and indicated at 1103 and 1107) with target nucleic acid to be sequenced 1105 and 1109 (indicated by "B"s). A first anchor probe/sequencing probe complex is indicated at 1104, with the sequencing probe portion at 1112 and the ligation indicated by a ".". A second anchor probe/sequencing probe complex is indicated at 1108, with the sequencing probe portion at 1114 and the ligation between the two probes indicated by a ".". All sequencing probes may come from the same set of sequencing probes, shown here as 1120. Invader oligonucleotides are indicated at 1106 and 1110. In FIG. 5, "G", "T", "A" and "C" denote specific sequences, "N"s are universal or degenerate bases, n is equal to zero to 10, and C1, C2, C3 and C4 correspond to four different colored labels, e.g., fluorophores. Though only two adaptors are shown, multiple bases from multiple adaptors (rather than only the two seen here) may be interrogated at one time in this multiplexed cPAL reaction. To determine which sequencing probe is positive for each anchor probe, a discriminative removal of each anchor probe/sequencing probe complex is used using displacement (de-hybridization from the library construct) by invader oligonucleotides.

Invader oligonucleotides are identical or substantially identical to portions of the adaptors in the library constructs, and are complementary to the anchor probes. The invader oligonucleotides invade and destabilize the hybrid between the anchor probe/sequencing probe and the adaptor/target nucleic acid in the library construct 1102. Invader oligonucleotides can be structured in a number of ways to be disruptive of the anchor probe/sequencing probe:adaptor/target nucleic acid hybrids. For example, the invader oligonucleotides may have greater homology and/or have a longer stretch of homology to the anchor probes than do the adaptors. In some aspects, the anchor probe may include an overhang on the opposite end of the strand from the ligation site with the sequencing probe that is not complementary to the adaptor, but is complementary to the invader oligonucleotide. Also, the anchor probes may be engineered to have less than perfect homology to the adaptors, yet have perfect homology with the invader oligonucleotides. In yet another alternative, the invader oligonucleotides may employ PNA or LNA chemistry to make the hybrids with the anchor probes/sequencing probes more stable. In preferred aspects such as shown here, the invader oligonucleotides comprise degenerative bases (designated $N_n$) that provide homology to the sequencing probe ligated to the anchor probe allowing for increased homology to the anchor probe/sequencing probe complex, further destabilizing the anchor probe/sequencing probe:adaptor/target nucleic acid hybrid.

In methods using sequencing probe sets as shown in FIG. 11, anchor probes are allowed to hybridize to the adaptors in library constructs after which the set of sequencing probes is added, allowed to hybridize to the target nucleic acid, and the sequencing probes are then ligated to the adjacently-hybridized anchor probes. An extensive wash is performed to eliminate unligated sequencing probes. In this example, one sequencing probe should ligate to each anchor probe. An image is then taken. In a hypothetical where an A sequencing probe from the set of sequencing probes hybridized to the target nucleic acid and ligated to the anchor probe at the 5' end of the library construct (producing structure 1104) and a C sequencing probe from the set of sequencing probes hybridized to the target nucleic acid and ligated to the anchor probe at the 3' end of the library construct (producing structure 1108), the first image would show a C1+C3 signal. Next, a first invader oligonucleotide (e.g., that shown at 1106) is added to the sequencing mix under conditions that allow the invader oligonucleotide to destabilize the hybrid between the anchor probe/sequencing probe 1104 and the library construct 1102. A wash is then performed, removing the hybridized anchor probe/sequencing probe 1104 and the invader oligonucleotide 506 from the target nucleic acid. When the next image is then taken, only a C3 signal remains, indicating that there was a T immediately adjacent 3' to the 5' adaptor 1103 and that there is a G immediately adjacent 5' to the 3' adaptor 1107.

As an alternative to using four fluorophores, in certain aspects of the present invention, two fluorophores may be used to read four bases. For example, a probe set such as Probe A-C1, Probe C C1+C2, Probe G-no fluorophore and Probe T-C2 is useful in such techniques where, for example, the A probe is labeled with a first fluorophore, the T probe is labeled with a second fluorophore, the C probe is labeled with both the first fluorophore and the second fluorophore, and the G probe is not labeled such that a G is deduced if there is no fluorescence emitted. In addition, a probe set may allow for the reading of two bases at a time from two different adaptors with two different sequencing probe sets. In such a scheme, the discrimination of the invader oligonucleotide coupled with the use of different labels for sequencing from different adaptors increases the confidence level of the sequence read. For example, in first probe set the A probe may be labeled with a first fluorophore, the T probe may be labeled with a second fluorophore, the C probe may be labeled with both the first fluorophore and the second fluorophore, and the G probe may not be labeled such that a G is deduced if there is no fluorescence emitted from either the first fluorophore or the second fluorophore (e.g., for a set comprising sequencing probes interrogating the second base from the ligation junction, 3' to 5': NANNNN-C1, NCNNNNC1C2, NTNNNNC2, and NGNNNN). For the 3' set, the A probe is labeled with a third fluorophore, the T probe is labeled with a fourth fluorophore, the C probe is labeled with both the third fluorophore and the fourth fluorophore, and the G probe is not labeled such that a G is deduced if there is no fluorescence emitted from either the third fluorophore or the fourth fluorophore (e.g., for a set comprising sequencing probes interrogating the second base from the ligation junction, 3' to 5': C3-NNNNAN, C3C4NNNNCN, C4NNNNTN, and NNNNGN).

In yet another alternative, two bases may be read at a time from the same adaptor using the same anchor probe, the same invader oligonucleotide and two sequencing different probe sets, where, for example, in the first probe set the A probe is labeled with a first fluorophore, the T probe is labeled with a second fluorophore, the C probe is labeled with both the first fluorophore and the second fluorophore, and the G probe is not labeled such that a G is deduced if there is no fluorescence emitted from either the first fluorophore or the second fluorophore (e.g., for a set comprising sequencing probes interrogating the second base from the ligation junction, 3' to 5': NANNNN-C1, NCNNNNC1C2, NTNNNNC2, and NGNNNN), and where in the second probe set, A probe is labeled with a third fluorophore, the T probe is labeled with a fourth fluorophore, the C probe is labeled with both the third fluorophore and the fourth fluorophore, and the G probe is not labeled such that a G is deduced if there is no fluorescence emitted from either the first fluorophore or the second fluorophore (e.g., for a set comprising sequencing probes interrogating the second base from the ligation junction, 3' to 5': NNANNN-C1, NNCNNNC1C2, NNTNNNC2, and NNGNNN). Again, such an approach reduces the number of hybridization/ ligation cycles and the number of images in half, providing a near two-fold savings in cost and a two-fold savings in time. A preferred approach is to not score (label) the G probe, as G is known to have cross talk with A and T probes, on the other hand, the C probe has been observed to have the least cross talk, such that preferably it is the C probe that is labeled with two fluorophores.

Figure 7:
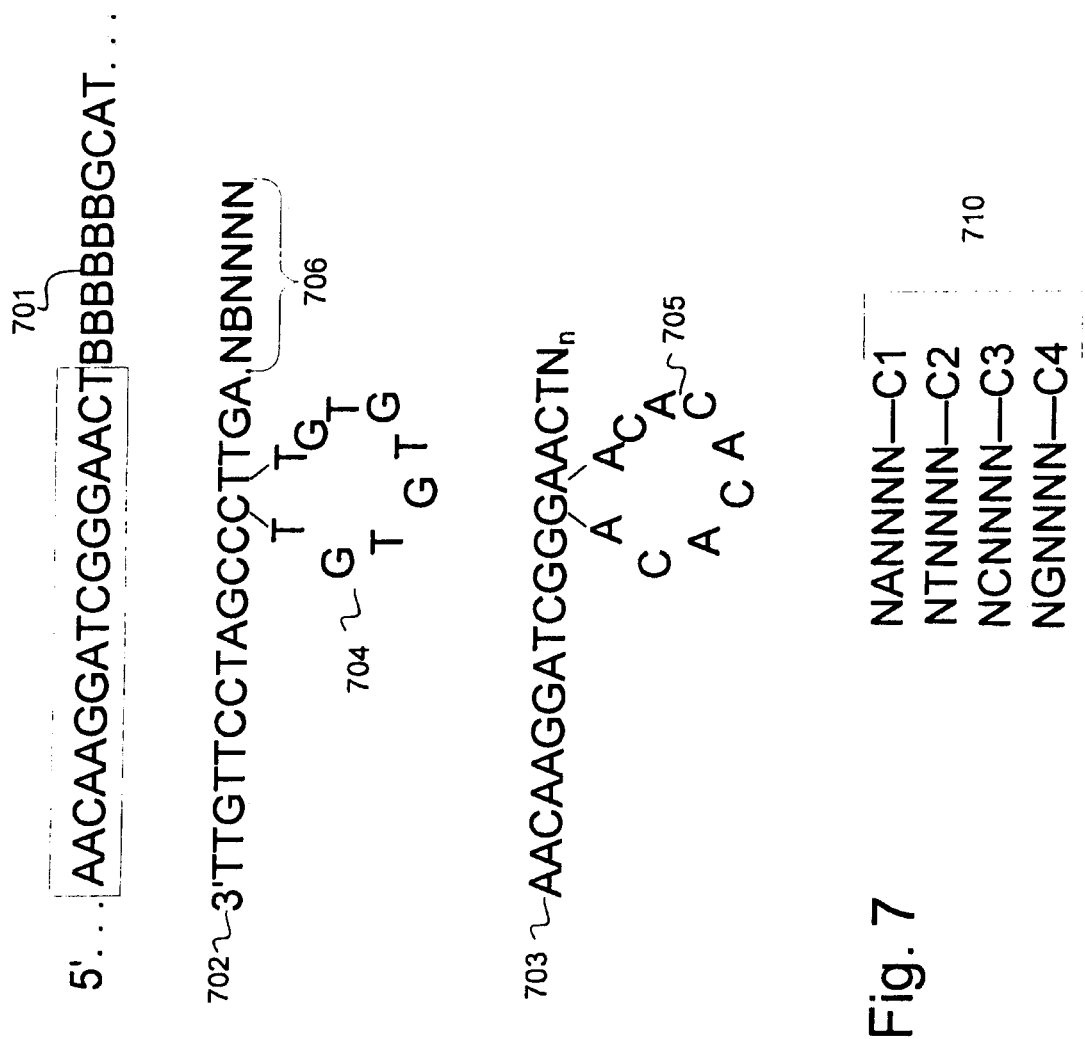
FIG. 7 is a schematic illustration of an embodiment of sequencing methods of the invention. Sequence legend: 701 (SEQ ID NO:21); 702 (SEQ ID NO:22); 703 (SEQ ID NO:23).

As with FIG. 11, FIG. 7 is a schematic illustration of yet another embodiment of cPAL sequencing, using anchor probes, sequencing probes and invader oligonucleotides. A portion of a library construct is shown at 701, having one adaptor (shaded) with target nucleic acid to be sequenced (indicated by "B"s). An anchor probe/sequencing probe complex is indicated at 702, with the sequencing probe portion at 606 and the ligation indicated by a ".". Although only one adaptor, anchor probe/sequencing probe complex and one invader oligonucleotide are shown, it should be understood that, as in FIG. 11, two, four or more sets of probes and invaders may be used in a multiplexed reaction. As in FIG. 7, all sequencing probes may come from the same set of sequencing probes, shown here as 710. The invader oligonucleotide is indicated at 703. As before, "G", "T", "A" and "C" denote specific sequences, "N"s are universal or degenerate bases, n is equal to zero to 10, and C1, 21, C2, C3 and C4 correspond to four different colored labels, e.g., fluorophores. As in FIG. 11, in FIG. 7 a discriminative removal of each anchor probe/sequencing probe ligated structure 702 is used using displacement by invader oligonucleotides 703 to determine which sequencing probe is ligated to which anchor probe; however, the anchor probe and invader oligonucleotide in this example have loops (704 and 705, respectively) that are complementary to one another, but that do not have homology to the adaptor within the library construct. The loops increase the relative homology of the anchor probe/sequencing probe to the invader oligonucleotide, and decrease the relative homology of the anchor probe/sequencing probe to the adaptor and target nucleic acid portions of the library construct. In addition, as described infra, the loops may be useful for other purposes as well. In addition, the invader probe includes a series of degenerative bases (indicated by "$N_n$") that bind with the sequencing probe portion of the anchor probe/sequencing probe complex further destabilizing the hybrid with the library construct.

In methods using anchor probes, sequencing probe sets and invader oligonucleotides as shown here in FIG. 7—as in FIG. 11—anchor probes are allowed to hybridize to the adaptors in library constructs after which the set of sequencing probes is added, allowed to hybridize to the target nucleic acid, and the sequencing probes are then ligated to adjacently hybridized anchor probes. An extensive wash is performed to eliminate unligated sequencing probes. In the aspect shown here, one sequencing probe should ligate to each anchor probe. An image is then taken. In a hypothetical where an A sequencing probe from the set of sequencing probes hybridized to the target nucleic acid and ligated to the anchor probe (to produce structure 702), and, for example, a T sequencing probe from the set of sequencing probes hybridized to the target nucleic acid and ligated to another anchor probe (not shown) and another A sequencing probe from the set of sequencing probes hybridized to the target nucleic acid and ligated to yet another anchor probe (not shown), the first image would show a C1 (x2)+C2 signal. A first invader oligonucleotide (e.g., shown at 603) is then added to the sequencing mix under conditions that allow the invader oligonucleotide to destabilize the hybrid between the anchor probe/sequencing probe 702 and the library construct 701 and to form a complex with the anchor probe/sequencing probe. A wash is then performed, removing the hybrid anchor probe/sequencing probe/invader oligonucleotide complex. When the next image is then taken, a C1+C2 signal remains, indicating that there was an A one base immediately adjacent the 3' end of the adaptor (shaded). A second round of invasion and imaging would remove, e.g., the C2-labeled sequencing probe, leaving only a C1 signal, showing that there was an A one base immediately adjacent the 3' end of another adaptor, and that there is a T one base immediately adjacent the 3' end of the last, uninvaded adaptor.

FIG. 8 is a schematic illustration of yet another exemplary library construct, anchor probe, sequencing probe and invader oligonucleotide useful in certain methods of the claimed invention. A portion of a library construct is shown at 812, having one adaptor (shaded) with target nucleic acid to be sequenced (indicated by "B"s). An anchor probe/sequencing probe complex is indicated at 814, with the sequencing probe portion at 816, the anchor probe portion at 813 (complementary to an adaptor in the library construct and to a portion of the target nucleic acid), a tail portion of the anchor probe at 815 (complementary to a tail portion 818 of the invader oligonucleotide, seen at 817) and a ligation site indicated by a ".". Although only one adaptor/invader oligonucleotide anchor probe/sequencing probe complex is shown, it should be understood that two, four or more sets of anchor probes and invader oligonucleotides may be used in a multiplexed reaction. All sequencing probes may come from the same set of sequencing probes, shown here as 830 (where the base to be interrogated is 4 bases from the ligation junction). The invader oligonucleotide has an anchor portion 819 (complementary to an adaptor in the library construct) and a tail portion 818. The invader oligonucleotide/anchor probe/sequencing probe complex is indicated at 811.

The anchor portion of the invader oligonucleotide 713 serves to stabilize the anchor probe/sequencing probe complex, so that the anchor probe may comprise a sequence of degenerate nucleotides that provides complementarity to a portion of the target nucleic acid, allowing for a shift of the site of ligation such that more bases can be read or read with more confidence further from the 5' end of the adaptor in the library construct. However, the greater complementarity between the invader oligonucleotide 817 and the adaptor probe/sequencing probe complex 714 will allow selective disruption of the adaptor probe/sequencing probe complex 814 from the library construct 812. As described previously, the anchor probes are allowed to hybridize to the adaptor probes in library constructs after which the set of sequencing probes is added, allowed to hybridize to the target nucleic acid, and the sequencing probes are then ligated to the adjacently-hybridized anchor probes. An extensive wash is performed to eliminate unligated sequencing probes. One sequencing probe should ligate to each anchor probe. An image is then taken. Next, a first invader oligonucleotide is added to the sequencing mix under conditions that allow the invader oligonucleotide to destabilize the hybrid between the anchor probe/sequencing probe and the library construct. A wash is then performed, removing the hybridized anchor probe/sequencing probe and the invader oligonucleotide from the target nucleic acid. When the next image is then taken, the label from the sequencing probe that has been selectively removed with the invader oligonucleotide should not be present.

As before, "G", "T", "A" and "C denote specific sequences, "N"s are universal or degenerate bases, n is equal to zero to 10, and C1, C2, C3 and C4 correspond to four different colored labels, e.g., fluorophores. "B"s in the library construct denote bases in the target nucleic acid that are to be sequenced. "B" in the sequencing probe denotes the interrogation base. In addition, the complementary tails in the anchor probe and the invader oligonucleotide, if desired, allow for the inclusion of cleavable sites (uracils, restriction sites, photocleavable sites) for specific removal of a anchor probe/sequencing probe complex, if desired.

In FIG. 8, the invader oligonucleotide 817 has a loop. In the aspect shown in FIG. 8, the loop in the invader oligonucleotide can be used to vary the properties of the invader oligonucleotide/anchor probe/sequencing probe complex. For example, as shown in FIG. 8, the loop can be used as a molecular "hook" such that an additional oligonucleotide (a "loop binding oligonucleotide" shown at 820) with complementarity to the loop in the tail portion of the invader oligonucleotide can bind the complex. The loop binding oligonucleotide can associate a non-nucleotide molecule(s) with the complex, such as an additional label (shown here at 821), a quenching moiety, a moiety that increases intensity of the label on the sequencing probe, a moiety that shifts the frequency of the label on the sequencing probe, an entity that allows for the complex to be captured (e.g., by biotin or another ligand, or a magnetic bead), and the like. The loop 705 in the invader oligonucleotide shown at 703 in FIG. 7 may serve similar functions.

For any of the sequencing methods described herein, methods of detecting and identifying sequencing probes are dependent on the types of labels used with those sequencing probes. Such labels and methods of detection are well known in the art and are described for example in U.S. application Ser. No. 11/679,124, now abandoned; Ser. No. 11/981,761, now U.S. Pat. No. 8,440,397; Ser. No. 11/981,661, now U.S. Pat. No. 8,722,326; Ser. No. 11/981,605, now U.S. Pat. No. 9,476,054; Ser. No. 11/981,793, now abandoned; Ser. No. 11/981,804, now abandoned; Ser. No. 11/451,691, now U.S. Pat. No. 8,445,194; Ser. No. 11/981,607, now U.S. Pat. No. 8,133,719; Ser. No. 11/981,767, now U.S. Pat. No. 8,445,196; Ser. No. 11/982,467, now U.S. Pat. No. 8,445,197; Ser. No. 11/451,692, now U.S. Pat. No. 7,709,197; Ser. No. 12/335,168, now U.S. Pat. No. 7,901,891; Ser. No. 11/541,225, now U.S. Pat. No. 7,960,104; Ser. No. 11/927,356, now U.S. Pat. No. 7,910,354; Ser. No. 11/927,388, now U.S. Pat. No. 7,910,302; Ser. No. 11/938,096, now U.S. Pat. No. 9,334,490; Ser. No. 11/938,106, now abandoned; Ser. No. 10/547,214, now U.S. Pat. No. 8,105,771; Ser. No. 11/981,730, now U.S. Pat. No. 7,910,304; Ser. No. 11/981,685, now U.S. Pat. No. 7,906,285; Ser. No. 11/981,797, now U.S. Pat. No. 8,278,039; Ser. No. 12/252,280, now U.S. Pat. No. 8,951,731; Ser. No. 11/934,695, now abandoned; Ser. No. 11/934,697, now abandoned; Ser. No. 11/934,703, now abandoned; Ser. No. 12/265,593, now U.S. Pat. No. 7,901,890; Ser. No. 12/266,385, now U.S. Pat. No. 7,897,344; Ser. No. 11/938,213, now abandoned; Ser. No. 11/938,221, now abandoned; Ser. No. 12/325,922, now U.S. Pat. No. 8,298,768; Ser. No. 12/329,365, now U.S. Pat. No. 8,415,099; Ser. No. 12/335,188, now U.S. Pat. No. 8,551,702; and Ser. No. 12/359,165, now abandoned, all of which are hereby incorporated by reference in their entirety for all purposes and particularly for all disclosure related to sequencing probes, labeled sequencing probes, methods of making labeled and unlabeled sequencing probes, and methods of detecting sequencing probes.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

The invention claimed is:

1. A method for determining nucleotide sequences from a plurality of different nucleic acid templates disposed at different array positions on a surface of a nucleic acid array, wherein each array position of the different array positions comprises a plurality of copies of one nucleic acid template of the plurality of different nucleic acid templates, wherein the method comprises conducting multiple cycles of sequencing-by-synthesis at each of the different array positions, wherein in each cycle of the multiple cycles of sequencing-by-synthesis, at each array position of the different array positions, a nucleotide selected from A, T, G and C anneals to a complementary nucleotide at a detection position of the plurality of copies of the one nucleic acid template, wherein at least three of the nucleotides selected from A, T, G and C are labeled with a fluorescent label that produces a fluorescent signal or at least three of the nucleotides selected from A, T, G and C are labeled with a luminescent label that produces a luminescent signal, wherein each cycle of the multiple cycles of sequencing-by-synthesis comprises (i) at each of a plurality of first array positions of the different array positions, binding a first nucleotide selected from A, T, G and C to a first complementary nucleotide at the detection position of the plurality of copies of the one nucleic acid template disposed at the first array positions, wherein the first nucleotide is complementary to the first complementary nucleotide, (ii) at each of a plurality of second array positions of the different array positions, binding a second nucleotide selected from A, T, G and C to a second complementary nucleotide at the detection position of the plurality of copies of the one nucleic acid template disposed at the second array positions, wherein the second nucleotide is complementary to the second complementary nucleotide, (iii) at each of a plurality of third array positions of the different array positions, binding a third nucleotide selected from A, T, G and C to a third complementary nucleotide at the detection position of the plurality of copies of the one nucleic acid template disposed at the third array positions, wherein the third nucleotide is complementary to the third complementary nucleotide, (iv) at each of a plurality of fourth array positions, binding a fourth nucleotide selected from A, T, G and C to a fourth complementary nucleotide at the detection position of the plurality of copies of the one nucleic acid template disposed at the fourth array positions, wherein the fourth nucleotide is complementary to the fourth complementary nucleotide, wherein each of the first nucleotide, the second nucleotide, the third nucleotide and the fourth nucleotide is one of A, T, G and C, wherein none of the first nucleotide, the second nucleotide, the third nucleotide and the fourth nucleotide is the same, wherein the plurality of first array positions, the plurality of second array positions, the plurality of third array positions and the plurality of fourth array positions are non-overlapping subsets of the different array positions on the surface of the nucleic acid array;

wherein the first nucleotide, the second nucleotide, the third nucleotide and the fourth nucleotide are labeled with the same fluorescent label or luminescent label but produce fluorescent or luminescent signals having different intensities, or wherein three of the first nucleotide, the second nucleotide, the third nucleotide and the fourth nucleotide are labeled with the same fluorescent label or luminescent label but produce fluorescent or luminescent signals having different intensities and one of the first nucleotide, the second nucleotide, the third nucleotide and the four nucleotide has no fluorescent label or luminescent label, wherein the first nucleotide, the second nucleotide, the third nucleotide and the fourth nucleotide are identified and distinguished from each other based on intensities of their fluorescent or luminescent signals, and (v) determining whether a complementary nucleotide at a detection position of the plurality of copies of the one nucleic acid template at each of the plurality of first array positions, the plurality of second array positions, the plurality of third array positions and the plurality of fourth array positions is A, T, G or C, by detecting an intensity of fluorescent or luminescent signal at each of the plurality of first array positions, the plurality of second array positions, the plurality of third array positions and the plurality of fourth array positions.

2. The method of claim 1, wherein the nucleic acid array is a DNA nanoball array.

3. The method of claim 1, wherein the first nucleotide is A.

4. The method of claim 1, wherein the first nucleotide is T.

5. The method of claim 1, wherein the first nucleotide is G.

6. The method of claim 1, wherein the first nucleotide is C.

* * * * *

SEQUENCE LISTING

```
<160> NUMBER OF SEQ ID NOS: 26

<210> SEQ ID NO 1
<211> LENGTH: 44
<212> TYPE: DNA
<213> ORGANISM: Artificial Sequence
<220> FEATURE:
<223> OTHER INFORMATION: Synthetic DNA polynucleotide

<400> SEQUENCE: 1
acttcagaac cgcaatgcac gatacgtctc gggaacgctg aaga            44

<210> SEQ ID NO 2
<211> LENGTH: 56
<212> TYPE: DNA
<213> ORGANISM: Artificial Sequence
<220> FEATURE:
<223> OTHER INFORMATION: Synthetic DNA polynucleotide

<400> SEQUENCE: 2
ggctccagcg gctaacgata gctcgagctc gagcaatgac gtctcgactc agcaga      56

<210> SEQ ID NO 3
<211> LENGTH: 56
<212> TYPE: DNA
<213> ORGANISM: Artificial Sequence
<220> FEATURE:
<223> OTHER INFORMATION: Synthetic DNA polynucleotide

<400> SEQUENCE: 3
actgctgacg tactgcgaga agctcgagct cgagcgactg cgcttcgact ggagac      56

<210> SEQ ID NO 4
<211> LENGTH: 68
<212> TYPE: DNA
<213> ORGANISM: Artificial Sequence
<220> FEATURE:
<223> OTHER INFORMATION: Synthetic DNA polynucleotide

<400> SEQUENCE: 4
aagtcggagg ccaagcggtc ttaggaagac aagctcgagc tcgagcgatc gggccgtacg   60
tccaactt                                                            68

<210> SEQ ID NO 5
<211> LENGTH: 14
<212> TYPE: DNA
<213> ORGANISM: Artificial Sequence
<220> FEATURE:
<223> OTHER INFORMATION: Synthetic DNA polynucleotide

<400> SEQUENCE: 5
gctcgagctc gagc             14

<210> SEQ ID NO 6
```

```
<211> LENGTH: 15
<212> TYPE: DNA
<213> ORGANISM: Artificial Sequence
<220> FEATURE:
<223> OTHER INFORMATION: Synthetic DNA polynucleotide

<400> SEQUENCE: 6
gatcagtcga tctca                                                    15

<210> SEQ ID NO 7
<211> LENGTH: 56
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (55)..(56)
<223> OTHER INFORMATION: n is a, c, g, or t

<400> SEQUENCE: 7
gctccagcgg ctaacgatgc tcgagctcga gcaatgacgt ctcgactcag cagann       56

<210> SEQ ID NO 8
<211> LENGTH: 57
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (56)..(57)
<223> OTHER INFORMATION: n is a, c, g, or t

<400> SEQUENCE: 8
tctccagtcg aagcgcagtc gctcgagctc gagcttctcg cagtacgtca gcagtnn      57

<210> SEQ ID NO 9
<211> LENGTH: 67
<212> TYPE: DNA
<213> ORGANISM: Artificial Sequence
<220> FEATURE:
<223> OTHER INFORMATION: Synthetic DNA polynucleotide

<400> SEQUENCE: 9
agtcggaggc caagcggtct taggaagaca agctcgagct cgagcgatcg ggccgtacgt   60
ccaactt                                                             67

<210> SEQ ID NO 10
<211> LENGTH: 35
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (5)..(20)
<223> OTHER INFORMATION: n is a, c, g, or t

<400> SEQUENCE: 10
gagtnnnnnn nnnnnnnnnn tgagatcgac tgatc                              35

<210> SEQ ID NO 11
<211> LENGTH: 47
<212> TYPE: DNA
<213> ORGANISM: Artificial Sequence
<220> FEATURE:
<223> OTHER INFORMATION: Synthetic DNA polynucleotide
```

```
<220> FEATURE:
<221> NAME/KEY: misc_feature
<222> LOCATION: (1)..(20)
<223> OTHER INFORMATION: n is a, c, g, or t

<400> SEQUENCE: 11
nnnnnnnnnn nnnnnnnnnn gatcatcgtc agcagtcgcg tagctag          47

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA polynucleotide

<400> SEQUENCE: 12
gctacgcgac tgctgacgat gatc                                   24

<210> SEQ ID NO 13
<211> LENGTH: 35
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (28)..(31)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t

<400> SEQUENCE: 13
ctagctcagc gactgctgca gatgatcnnn ncnnn                       35

<210> SEQ ID NO 14
<211> LENGTH: 47
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t

<400> SEQUENCE: 14
nnnnnnnnnn nnnnngnnnn gatcatcgtc agcagtcgcg tagctag          47

<210> SEQ ID NO 15
<211> LENGTH: 44
<212> TYPE: DNA
<213> ORGANISM: Artificial Sequence
<220> FEATURE:
<223> OTHER INFORMATION: Synthetic DNA polynucleotide

<400> SEQUENCE: 15
tcttcagcgt tcccgagacg tatcgtgcat tgcggttctg aagt             44

<210> SEQ ID NO 16
<211> LENGTH: 38
<212> TYPE: DNA
<213> ORGANISM: Artificial Sequence
<220> FEATURE:
```

```
<223> OTHER INFORMATION: Synthetic DNA polynucleotide
<220> FEATURE:
<221> NAME/KEY: misc_feature
<222> LOCATION: (11)..(19)
<223> OTHER INFORMATION: n is a, c, g, or t
<220> FEATURE:
<221> NAME/KEY: misc_feature
<222> LOCATION: (30)..(38)
<223> OTHER INFORMATION: n is a, c, g, or t

<400> SEQUENCE: 16
gggggaggcc nnnnnnnnnc cttccccggn nnnnnnn                              38

<210> SEQ ID NO 17
<211> LENGTH: 16
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(6)
<223> OTHER INFORMATION: n is a, c, g, or t

<400> SEQUENCE: 17
nnnnnnggcc tccccc                                                     16

<210> SEQ ID NO 18
<211> LENGTH: 11
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (11)..(11)
<223> OTHER INFORMATION: n is a, c, g, or t

<400> SEQUENCE: 18
gggggaggcc n                                                          11

<210> SEQ ID NO 19
<211> LENGTH: 16
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(6)
<223> OTHER INFORMATION: n is a, c, g, or t

<400> SEQUENCE: 19
nnnnnnccgg ggaagg                                                     16

<210> SEQ ID NO 20
<211> LENGTH: 11
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (11)..(11)
<223> OTHER INFORMATION: n is a, c, g, or t

<400> SEQUENCE: 20
ccttccccgg n                                                          11
```

```
<210> SEQ ID NO 21
<211> LENGTH: 27
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (18)..(23)
<223> OTHER INFORMATION: n is a, c, g, or t

<400> SEQUENCE: 21
aacaaggatc gggaactnnn nnngcat                                    27

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (1)..(6)
<223> OTHER INFORMATION: n is a, c, g, or t

<400> SEQUENCE: 22
nnnnnnagtt tgtgtgtgtc ccgatccttg tt                              32

<210> SEQ ID NO 23
<211> LENGTH: 27
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (27)..(27)
<223> OTHER INFORMATION: n is a, c, g, or t

<400> SEQUENCE: 23
aacaaggatc gggacacaca caaactn                                    27

<210> SEQ ID NO 24
<211> LENGTH: 35
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (18)..(35)
<223> OTHER INFORMATION: n is a, c, g, or t

<400> SEQUENCE: 24
aacaaggatc gggaactnnn nnnnnnnnn nnnnn                            35

<210> SEQ ID NO 25
<211> LENGTH: 26
<212> TYPE: DNA
<213> ORGANISM: Artificial Sequence
<220> FEATURE:
<223> OTHER INFORMATION: Synthetic DNA polynucleotide
<220> FEATURE:
<221> NAME/KEY: misc_feature
<222> LOCATION: (17)..(26)
<223> OTHER INFORMATION: n is a, c, g, or t

<400> SEQUENCE: 25
cctggtcgat tcttgannnn nnnnnn                                     26
```

```
<210> SEQ ID NO 26
<211> LENGTH: 33
<212> TYPE: DNA
<213> ORGANISM: Artificial Sequence
<220> FEATURE:
<223> OTHER INFORMATION: Synthetic DNA polynucleotide

<400> SEQUENCE: 26
aacaaggatc ggaattatat atatacgagc agg                                    33
```